(12) United States Patent
Suzuki et al.

(10) Patent No.: US 8,591,417 B2
(45) Date of Patent: Nov. 26, 2013

(54) ULTRASONIC DIAGNOSTIC APPARATUS

(75) Inventors: Takao Suzuki, Yokohama (JP); Hisashi Hagiwara, Yokohama (JP); Yoshinao Tannaka, Aiko-gun (JP); Yoshinobu Watanabe, Yokohama (JP)

(73) Assignee: Panasonic Corporation, Osaka (JP)

( * ) Notice: Subject to any disclaimer, the term of this patent is extended or adjusted under 35 U.S.C. 154(b) by 710 days.

(21) Appl. No.: 10/556,880

(22) PCT Filed: May 19, 2004

(86) PCT No.: PCT/JP2004/007110
§ 371 (c)(1),
(2), (4) Date: Nov. 15, 2005

(87) PCT Pub. No.: WO2004/103185
PCT Pub. Date: Dec. 2, 2004

(65) Prior Publication Data
US 2007/0055149 A1    Mar. 8, 2007

(30) Foreign Application Priority Data

May 20, 2003  (JP) .................................. 2003-142481
Oct. 3, 2003   (JP) .................................. 2003-346182

(51) Int. Cl.
*A61B 8/00* (2006.01)
(52) U.S. Cl.
USPC ........... 600/437; 600/438; 600/440; 600/443; 600/447; 600/587
(58) Field of Classification Search
USPC .................. 600/437–438, 440, 443, 447, 587; 73/787
See application file for complete search history.

(56) References Cited

U.S. PATENT DOCUMENTS 5,524,636 A * 6/1996 Sarvazyan et al. ............. 600/587
5,678,565 A * 10/1997 Sarvazyan ..................... 600/587
(Continued)

FOREIGN PATENT DOCUMENTS

JP  10-5226    1/1998
JP  10-262970  10/1998
(Continued)

OTHER PUBLICATIONS

Chinese Office Action, dated Aug. 22, 2008.

*Primary Examiner* — Long V. Le
*Assistant Examiner* — Bo J Peng
(74) *Attorney, Agent, or Firm* — Hamre, Schumann, Mueller & Larson, P.C.

(57) ABSTRACT

There are provided a transmission unit (102) and a reception unit (103) for transmitting and receiving an ultrasonic wave with respect to a subject, a tissue tracing unit (115) for analyzing a received signal to trace the movement of a tissue of the subject, and a property detection unit (120) for detecting a property concerning the movement of the tissue of the subject. The property detection unit (120) subjects either one of the received signal, a Doppler shift, and the movement of the tissue of the subject to signal processing, detects a property concerning the movement of the tissue of the subject that is in synchronization with a heartbeat, and generates an initializing pulse based on the detected property. The tissue tracing unit (115) is initialized by the initializing pulse. It is possible to obtain a distribution image of an elastic modulus of the tissue of the subject as well as a tomographic image of the subject with a simple operation of only applying a probe to the subject without the necessity for a special connection between the subject and the device.

22 Claims, 21 Drawing Sheets

(56) References Cited

U.S. PATENT DOCUMENTS

| | | | |
|---|---|---|---|
| 5,840,028 A * | 11/1998 | Chubachi et al. | 600/437 |
| 5,953,439 A * | 9/1999 | Ishihara et al. | 382/107 |
| 6,224,553 B1 * | 5/2001 | Nevo | 600/437 |
| 6,423,006 B1 | 7/2002 | Banjanin | |
| 6,508,768 B1 * | 1/2003 | Hall et al. | 600/443 |
| 6,517,485 B2 * | 2/2003 | Torp et al. | 600/438 |
| 7,050,610 B2 * | 5/2006 | Chen et al. | 382/128 |
| 2002/0072674 A1 * | 6/2002 | Criton et al. | 600/454 |
| 2002/0177775 A1 | 11/2002 | Torp et al. | |
| 2003/0013964 A1 * | 1/2003 | Bjaerum et al. | 600/443 |
| 2003/0083578 A1 * | 5/2003 | Abe et al. | 600/447 |
| 2003/0125624 A1 | 7/2003 | Shiki | |
| 2003/0187350 A1 | 10/2003 | Omiya | |
| 2005/0187470 A1 * | 8/2005 | Kubota et al. | 600/437 |

FOREIGN PATENT DOCUMENTS

| | | |
|---|---|---|
| JP | 2000-229078 | 8/2000 |
| JP | 2001-070303 | 3/2001 |
| JP | 2001-238884 | 9/2001 |
| JP | 2001-286471 | 10/2001 |
| JP | 2003-290225 | 10/2003 |

* cited by examiner

ULTRASONIC DIAGNOSTIC APPARATUS

TECHNICAL FIELD

The present invention relates to an ultrasonic diagnostic apparatus that creates a distribution image of a tissue property such as an elastic modulus of a tissue of a subject.

BACKGROUND ART

Conventional ultrasonic diagnostic apparatuses irradiate a subject with an ultrasonic wave and convert the intensity of a reflected echo signal thereof into the luminance of a corresponding pixel, thereby obtaining a tomographic image of the structure of the subject. Further, in recent years, it is attempted to obtain an elastic modulus of a subject based on the movement of the subject measured precisely by analyzing the phase of a reflected echo signal.

For example, JP 10(1998)-5226 A describes a method of tracing a tissue with high accuracy by determining momentary positions of a subject using both the amplitude and the phase of a demodulation output signal of a reflected echo signal, thereby capturing micro vibrations on a large amplitude displacement motion caused by heartbeats. The method of tracing a tissue of a subject described in JP 10(1998)-5226 A will be described with reference to FIG. 21.

In FIG. 21, y(t) and y(t+ΔT) represent received signals of ultrasonic pulses transmitted at an interval of ΔT in the same direction of a subject. Herein, t represents a time. Assuming that the pulse transmission time is t=0, the reception time t1 of a received signal from a certain depth x1 is expressed as follows: t1=x1/(C/2), where C represents a sound velocity. Assuming that the phase displacement between y(t1) and y(t1+ΔT) is represented by Δθ, and the center frequency of the ultrasonic wave in the vicinity of the time t1 is represented by f, the movement Δx of x1 during the period ΔT is expressed as follows:

$$\Delta x = -C \cdot \Delta\theta / 4\pi f \quad (1)$$

By adding Δx to x1, the position x1' after ΔT second can be obtained as follows:

$$x1' = x1' + \Delta x \quad (2)$$

By repeating this operation, it is possible to trace the same region x1 of the subject.

Further, as an example of an advanced form of the method described in JP 10(1998)-5226 A, JP 2000-229078 A describes a method of obtaining a local elastic modulus by precisely tracing a large amplitude displacement motion caused by heartbeats on each of an inner surface and an outer surface of a blood vessel wall. According to this method, the motion velocity of micro vibrations superimposed on a large amplitude displacement motion is obtained, a strain of a blood vessel wall is measured based on a difference in velocity, and a local elastic modulus is obtained based on the strain and a difference in blood pressure. This method also makes it possible to display a space distribution of the elastic modulus visually. The method of calculating an elastic modulus described in JP 2000-229078 A will be described with reference to FIGS. 22A and 22B.

FIG. 22A shows a blood vessel 300 with an atheroma 303 by way of example. A probe 101 irradiates a subject 304 with an ultrasonic wave and receives an echo from the blood vessel 300, particularly an artery. Measurement points A and B are set on a blood vessel wall, and received signals from the measurement points A and B are analyzed by the above-mentioned method, whereby the movement (position) of each of the measurement points A and B is traced.

As shown by an ECG waveform in FIG. 22B, the artery contracts and expands repeatedly in response to heartbeats. Accordingly, the movements of the measurement points A and B are periodic as shown by tracing waveforms TA and TB, respectively. That is to say, the movements of the measurement points A and B follow the movement of the blood vessel wall that expands rapidly when the heart contracts and contracts gradually when the heart expands. A waveform W(=TB−TA) showing a change in the thickness between the measurement points A and B can be obtained from the tracing waveforms TA and TB. Assuming that the change amount of the thickness change waveform W is represented by ΔW, and the reference thickness when the measurement points are initialized is represented by Ws, the strain ε between the measurement points A and B is expressed as follows:

$$\epsilon = \Delta W / Ws \quad (3)$$

Assuming that the difference in blood pressure at this time is represented by ΔP, the elastic modulus Er between the measurement points A and B can be obtained by the following equation:

$$Er = \Delta P / \varepsilon \quad (4)$$
$$= \Delta P \cdot Ws / \Delta W$$

By performing this operation with respect to a plurality of points on a tomographic image, a distribution image of the elastic modulus can be obtained.

However, in the method of tracing a tissue described in JP 10(1998)-5226 A, since a position change is added sequentially, errors that have occurred due to various causes such as noise and hand movement are accumulated, resulting in a decrease in tracing accuracy. In the method described in JP 2000-229078 A, in order to solve the above-mentioned problem, the tracing position is initialized regularly by an R wave detected from an electrocardiogram. However, in order to carry out an electrocardiogram, it is required to attach electrodes to at least three places of a subject and it takes time and labor to attach/detach the electrodes.

DISCLOSURE OF INVENTION

An object of the present invention is to provide an ultrasonic diagnostic apparatus that is capable of obtaining a tissue property such as a strain, an elastic modulus, and a viscosity coefficient with a simple operation of only applying a probe to a subject without the need for a special connection of an electrocardiograph, a phonocardiograph, or the like between the device and the subject. Another object of the present invention is to provide an ultrasonic diagnostic apparatus that is capable of tracing the movement of a tissue of a subject with accuracy.

In order to achieve the above-mentioned objects, an ultrasonic diagnostic apparatus according to a first basic configuration of the present invention includes: ultrasonic wave transmission and reception means for transmitting and receiving an ultrasonic wave with respect to a subject; tissue tracing means for analyzing a received signal to trace a movement of a tissue of the subject; and property detection means for detecting a property concerning the movement of the tissue of the subject based on the movement of the tissue of the subject being traced, and outputting a property detection signal, wherein the tissue tracing means is initialized based on the property detection signal.

An ultrasonic diagnostic apparatus according to a second basic configuration of the present invention includes: ultrasonic wave transmission and reception means for transmitting and receiving an ultrasonic wave with respect to a subject; tissue tracing means for analyzing a received signal to trace a movement of a tissue of the subject; and property detection means for detecting a property concerning the movement of the tissue of the subject based on an amplitude or a phase of the received signal in accordance with the movement of the tissue of the subject, and outputting a property detection signal, wherein the tissue tracing means is initialized based on the property detection signal.

An ultrasonic diagnostic apparatus according to a third basic configuration of the present invention includes: ultrasonic wave transmission and reception means for transmitting and receiving an ultrasonic wave with respect to a subject; tissue tracing means for analyzing a received signal to trace a movement of a tissue of the subject; Doppler signal processing means for detecting a Doppler shift of the received signal in accordance with the movement of the tissue of the subject being traced; and property detection means for detecting a property concerning the movement of the tissue of the subject based on the detected Doppler shift, and outputting a property detection signal, wherein the tissue tracing means is initialized based on the property detection signal.

According to any one of the first to third basic configurations, it is possible to trace a tissue of a subject accurately with a simple operation of only applying a probe to the subject without the necessity for a special connection between the subject and the device.

It is preferable that any one of the above-mentioned basic configurations further includes delay means for delaying the property detection signal for a predetermined delay time, wherein the tissue tracing means is initialized by the delayed property detection signal. According to this configuration, initialization is performed at a more appropriate timing, whereby the movement of a tissue of a subject can be detected with increased accuracy.

In this configuration, the predetermined delay time can be estimated from several immediately preceding intervals at which the property concerning the movement is detected. Consequently, in the case where a tissue of a subject is, for example, a blood vessel, the timing of initialization can be set immediately before an end stage of a blood vessel contraction period. Therefore, each time required for a change in the thickness of a blood vessel wall to be maximum or minimum from the timing of the initialization can be shortened, whereby a tissue property such as an elastic modulus can be obtained with high tracing accuracy.

An ultrasonic diagnostic apparatus according to a fourth basic configuration of the present invention includes: ultrasonic wave transmission and reception means for transmitting and receiving an ultrasonic wave with respect to a subject; delay means for delaying a received signal; tissue tracing means for analyzing at least the delayed received signal to trace a movement of a tissue of the subject; and property detection means for detecting a property concerning the movement of the tissue of the subject, and outputting a property detection signal, wherein the tissue tracing means is initialized based on the property detection signal.

It is possible that any one of the first to fourth basic configurations includes selection means for analyzing movements of a plurality of tissues of the subject to select one from the plurality of tissues of the subject, wherein the property detection means detects a property concerning a movement of the selected tissue of the subject, and outputs the property detection signal.

It is possible that any one of the first to fourth basic configurations further includes selection means for analyzing a plurality of received signals to select one from a plurality of tissues of the subject, wherein the property detection means detects a property concerning a movement of the selected tissue of the subject, and outputs the property detection signal.

It is possible that any one of the first to fourth basic configurations further includes selection means for analyzing Doppler shifts of a plurality of received signals to select one from a plurality of tissues of the subject, wherein the property detection means detects a property concerning a movement of the selected tissue of the subject, and outputs the property detection signal.

It is possible that any one of the first to fourth basic configurations further includes: means for calculating a tissue property of the subject such as a strain, a viscosity coefficient, and an elastic modulus based on the movement of the tissue of the subject; and selection means for analyzing the tissue property of the subject to select one from a plurality of tissues of the subject, wherein the property detection means detects a property concerning a movement of the selected tissue of the subject, and outputs the property detection signal.

In any one of the above-mentioned configurations, the property concerning the movement can be a property that is in synchronization with a heartbeat. Alternatively, the property concerning the movement can be a property that is in synchronization with pressure relaxation or vibration produced externally.

Further, it is preferable that any one of the above-mentioned configurations includes means for switching between an initializing operation by the initializing means and an initializing operation of initializing the tracing means by a signal that is in synchronization with a heartbeat, the signal being taken from means for measuring heartbeat information including an electrocardiogram or a cardiac sound. Consequently, it is possible to switch easily between a conventional initializing operation by an electrocardiogram and an initializing operation according to any one of the above-mentioned configurations depending upon the circumstances.

Further, it is possible that any one of the above-mentioned configurations further includes means for calculating a tissue property of the subject such as a strain and a viscosity coefficient based on movements of a plurality of tissues of the subject. Alternatively, it is possible that any one of the above-mentioned configurations further includes means for obtaining a strain of the tissue of the subject based on movements of a plurality of tissues of the subject, and calculating an elastic modulus of the tissue of the subject based on the strain and a blood pressure value that is taken from blood pressure measurement means.

DESCRIPTION OF THE INVENTION (Embodiment 1)

Figure 1:
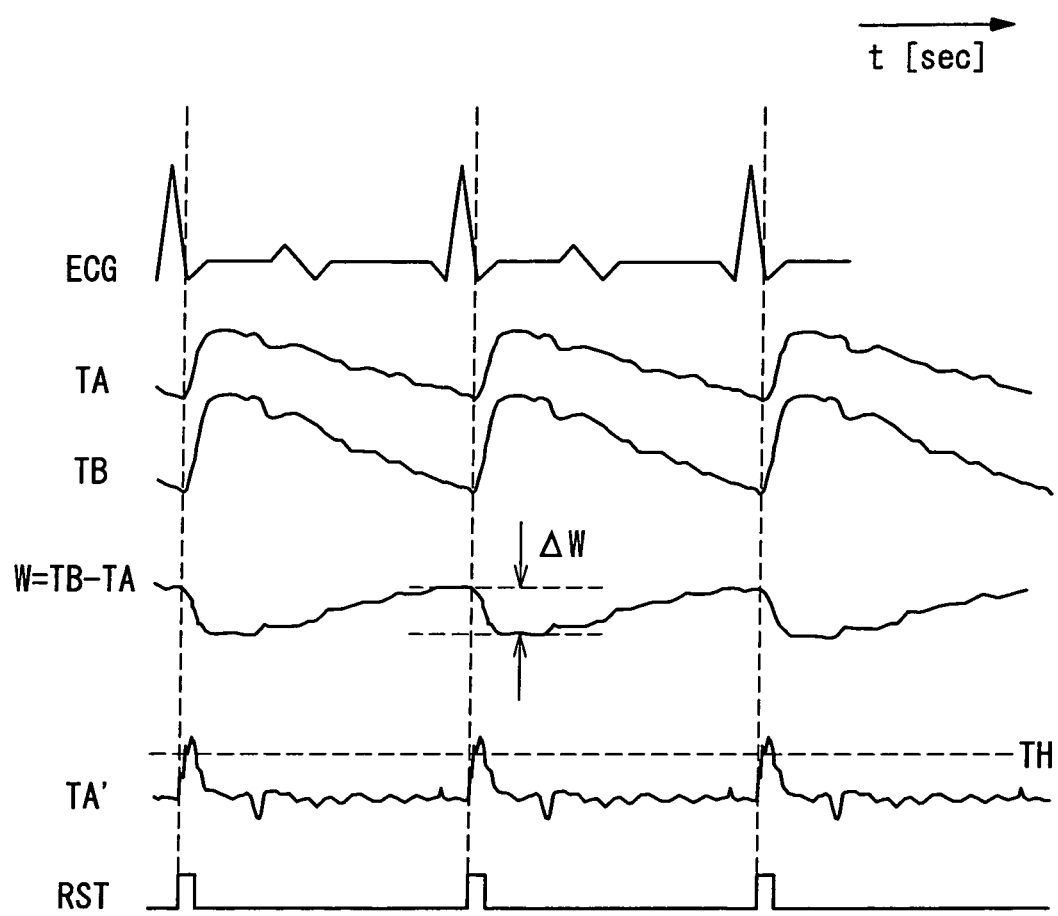
FIG. 1 is a diagram of waveforms of respective parts showing an operation of an ultrasonic diagnostic apparatus according to Embodiment 1 of the present invention.
Figure 22A:
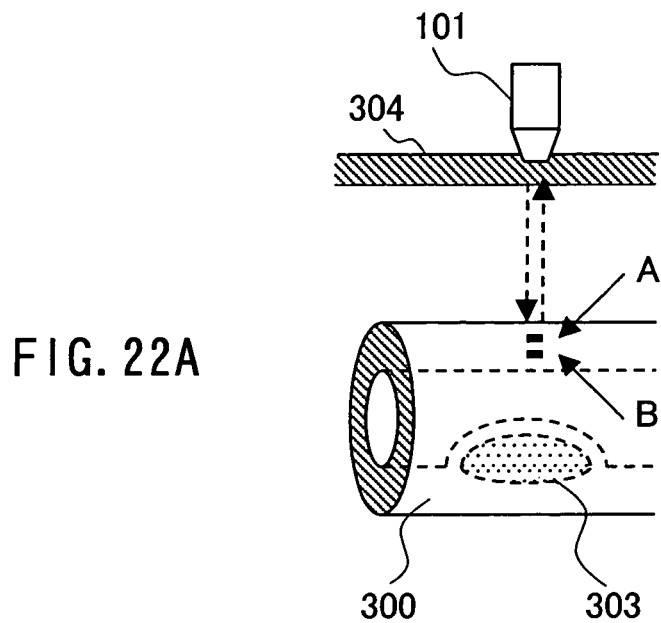
FIG. 22A is a schematic view showing places (measurement points) at which the movement of a tissue of a subject is traced according to a conventional example and the embodiments of the present invention.
Figure 22B:
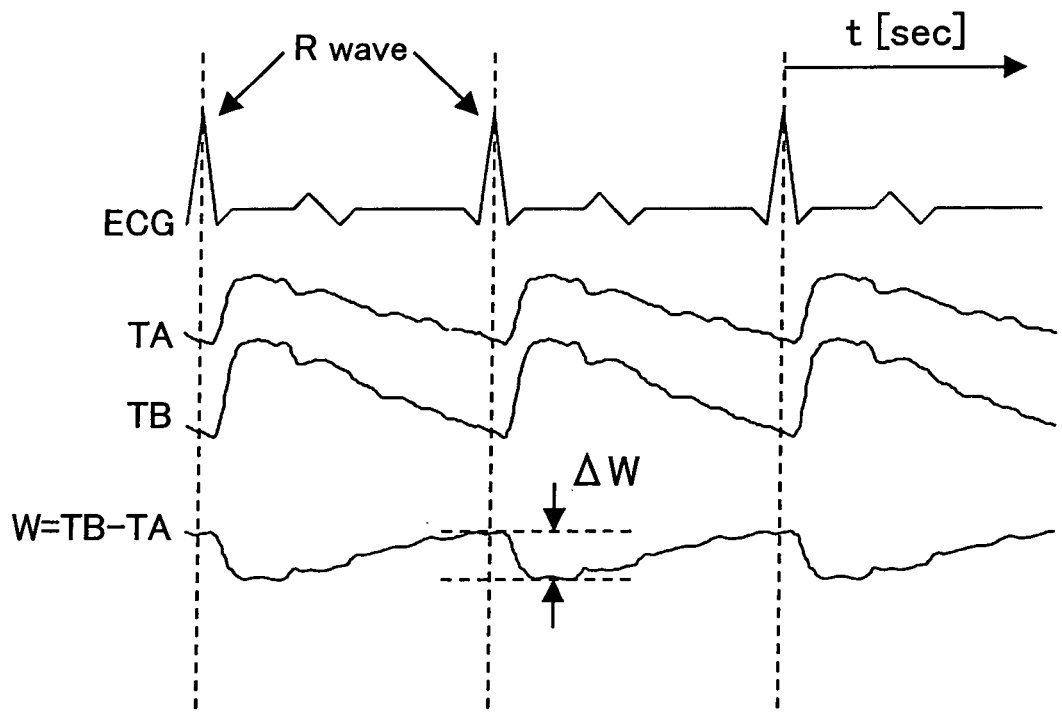
FIG. 22B is a waveform diagram for explaining a method of tracing a tissue of a subject according to the conventional example.

An operation of an ultrasonic diagnostic apparatus according to Embodiment 1 of the present invention will be described with reference to FIG. 1. FIG. 1 is a diagram of waveforms of respective parts showing an operation of the ultrasonic diagnostic apparatus according to the present embodiment. These waveforms are obtained when an ultrasonic wave is applied to a blood vessel of a subject as shown in FIG. 22A. In FIG. 1, ECG represents an electrocardiographic waveform, TA represents a tracing waveform at a measurement point A in FIG. 22A, and TB represents a tracing waveform at a measurement point B. W(=TB−TA) represents a thickness change waveform, TA' represents a differentiated waveform of TA, and RST represents an initializing pulse.

As described using the equations (1) and (2), the measurement points A and B are set on a blood vessel wall, and the phases of received signals are analyzed, whereby the movement of each of the measurement points A and B is traced. An artery contracts and expands repeatedly in response to heartbeats. Accordingly, the movements of the measurement points A and B are periodic as shown by the tracing waveforms TA and TB in FIG. 1, respectively. The waveform W showing a change in the thickness between the measurement points A and B can be obtained from the tracing waveforms TA and TB.

Assuming that the change amount of the thickness change waveform W is represented by $\Delta W$, and the reference thickness when the measurement points are initialized is represented by Ws as described above, the strain $\epsilon$ between the measurement points A and B is expressed as follows:

$$\epsilon = \Delta W / Ws$$

Assuming that the difference in blood pressure at this time is represented by $\Delta P$, the elastic modulus Er between the measurement points A and B can be obtained by the following equation:

$$Er = \Delta P / \epsilon = \Delta P \cdot Ws / \Delta W$$

By performing the operation and processing as described above with respect to a plurality of measurement points on a tomographic image, a distribution image of the elastic modulus indicating the hardness and softness of a tissue of a subject can be obtained.

Further, in the present embodiment, the measurement points A and B as tracing positions are initialized by using a change in the tracing waveform TA, i.e., the differentiated waveform TA' as shown in FIG. 1, while such initialization conventionally has been performed with an R wave detected from an electrocardiogram. More specifically, one initializing pulse RST is generated from the differentiated waveform TA' per one heartbeat, and the measurement positions A and B as tracing positions are initialized by the initializing pulse. In this case, the threshold value TH may be a constant value, a value as a certain percentage of the immediately preceding maximum value, or a dynamic value that decreases with time. In order to prevent the initializing pulse RST from being generated continuously, it is also effective to provide a dead time of several hundreds of milliseconds. In brief, it is important to generate one initializing pulse per one heartbeat reliably.

In the above-mentioned manner, a distribution image of the elastic modulus can be obtained with a simple operation of only applying a probe to a subject without the need for a special connection of an electrocardiograph or the like between the device and the subject.

In FIG. 1, the initialization is performed by using the tissue tracing waveform TA. However, a measurement point may be provided additionally for initialization. In such a case, the measurement point preferably is provided on a blood vessel wall, but may be provided on any tissues that move in synchronization with a heartbeat such as a tissue in the vicinity of a blood vessel.

According to the configuration in FIG. 1, the initialization is performed by using the differentiated waveform of the tissue tracing waveform. However, the present embodiment is not limited thereto, and various other information may be used as a property of a subject that is in synchronization with a heartbeat so as to obtain a property detection signal. For example, any information that moves in synchronization with a heartbeat is available such as the tissue tracing waveform itself, the thickness change waveform W, a change in the strain $\epsilon$, a pulse wave on a blood vessel, a blood flow velocity, a blood flow intensity, a pulse, a momentary blood pressure waveform, a cardiac sound, differentiated waveforms thereof, and the like.

Figure 2:
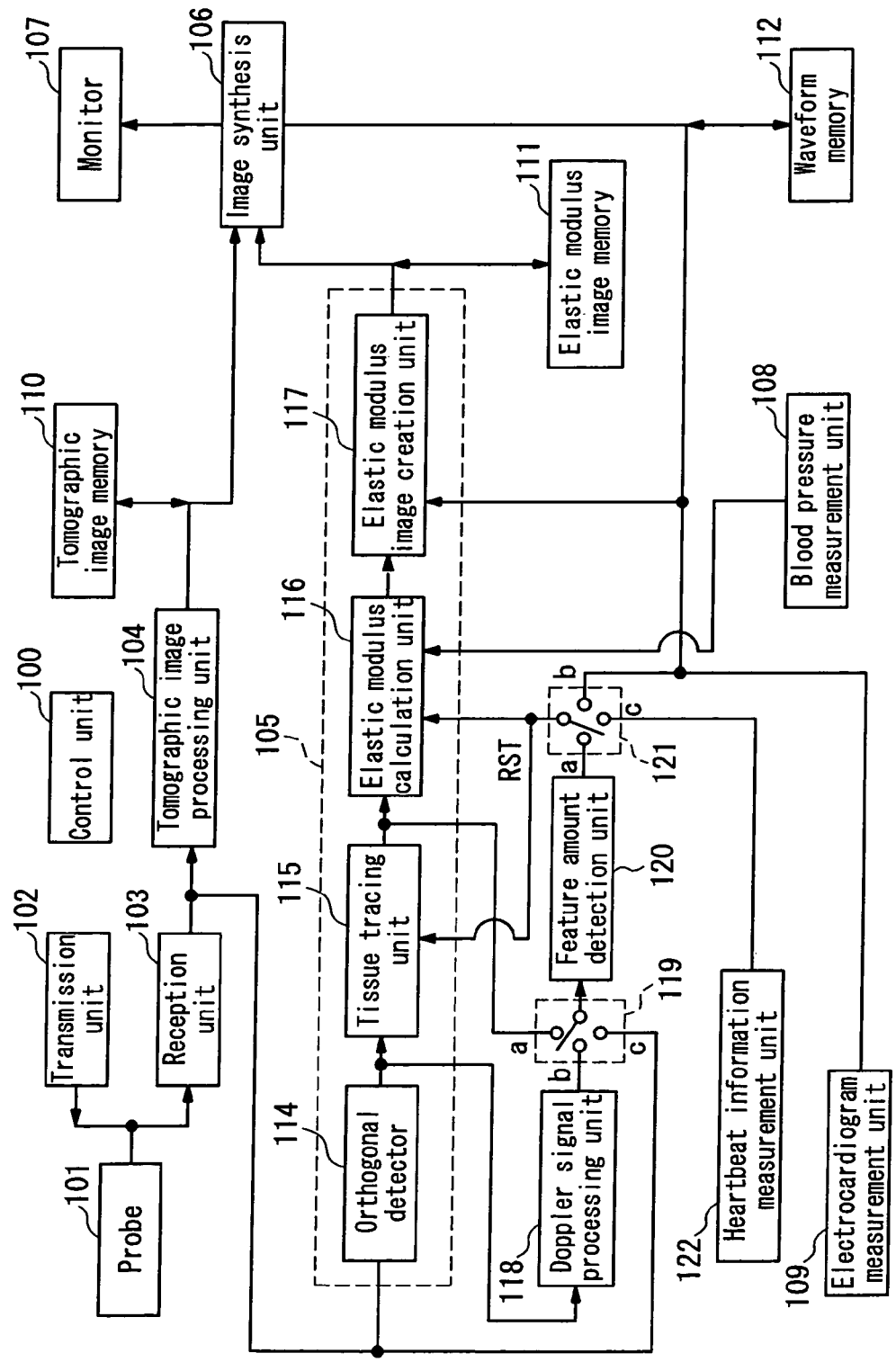
FIG. 2 is a block diagram of the ultrasonic diagnostic apparatus according to Embodiment 1.

Next, a specific configuration of the ultrasonic diagnostic apparatus that achieves the above-described operation will be described with reference to FIG. 2. FIG. 2 is a circuit block diagram showing an exemplary configuration of the ultrasonic diagnostic apparatus according to the present embodiment.

In FIG. 2, a control unit 100 controls the overall ultrasonic diagnostic apparatus. A transmission unit 102 generates a high-voltage transmission pulse for driving a probe 101 on receipt of instructions concerning a pulse width, a timing, the number of pulses, and the like from the control unit 100. The probe 101 converts the high-voltage transmission pulse from the transmission unit 102 into an ultrasonic wave to irradiate a subject with the ultrasonic wave and converts an ultrasonic echo reflected from an inside of the subject into an electronic signal. A reception unit 103 amplifies a received signal and detects an ultrasonic wave only from a predetermined position and direction. A tomographic image processing unit 104, which is constituted by a bandpass filter, a logarithmic compressor, a demodulator, and the like, mainly analyzes the amplitude of the received signal to create an image of the internal structure of the subject.

An elastic modulus distribution image processing unit 105, which is constituted by an quadrature demodulation unit 114, a tissue tracing unit 115, an elastic modulus calculation unit 116 as tissue property calculation means, and an elastic modulus distribution image creation unit 117, creates an image of a two-dimensional distribution of an elastic modulus. The quadrature demodulation unit 114 subjects the received signal to quadrature demodulation. The tissue tracing unit 115, which is one of the central components for tracing the movement of a tissue of a subject with accuracy in the present embodiment, mainly analyzes the phase of the received signal to trace the movement of a tissue. The elastic modulus calculation unit 116 calculates a strain of the tissue from a plurality of traced movements of the tissue, and calculates a local elastic modulus of the tissue based on a blood pressure value measured by a blood pressure measurement unit 108 and the strain. The elastic modulus distribution image creation unit 117 creates an image of a two-dimensional distribution of the elastic modulus.

A Doppler signal processing unit 118 analyzes a Doppler shift of the received signal to detect the movement of the tissue or a blood flow. A property detection unit 120 analyzes the amplitude or the phase of the one-dimensional received signal or the Doppler shift or a tissue tracing waveform obtained by analyzing the amplitude or the phase of the received signal, detects a property of the subject that is in synchronization with a heartbeat, and generates an initializing pulse for initializing the tissue tracing unit 115 as a property detection signal. In the present embodiment, since the one-dimensional signal before an image is created is used, a signal that is in synchronization with a heartbeat can be detected easily and accurately as compared with a method in which a signal that is in synchronization with a heartbeat is detected by analyzing an image. The initializing pulse is also a timing signal for calculating the elastic modulus in the elastic modulus calculation unit 116. A heartbeat information measurement unit 122 detects a property that is in synchronization with a heartbeat from a pulsimeter, a real time sphygmomanometer, a sphygmograph, or the like. A switch 119 selects an input signal to the property detection unit 120 from the outputs of the tissue tracing unit 115, the Doppler signal processing unit 118, and the reception unit 103. A switch 121 selects an initializing signal to the tissue tracing unit 115 from the outputs of the property detection unit 120, the heartbeat information measurement unit 122, and an electrocardiogram measurement unit 109.

An image synthesis unit 106 synthesizes the tomographic image, the distribution image of the elastic modulus, an electrocardiographic waveform, and the like and displays the synthesized image on a monitor 107. A tomographic image memory 110, an elastic modulus distribution image memory 111, and a waveform memory 112 record the tomographic image, the distribution image of the elastic modulus, and the electrocardiographic waveform or a cardiac sound waveform, respectively.

Figure 3:
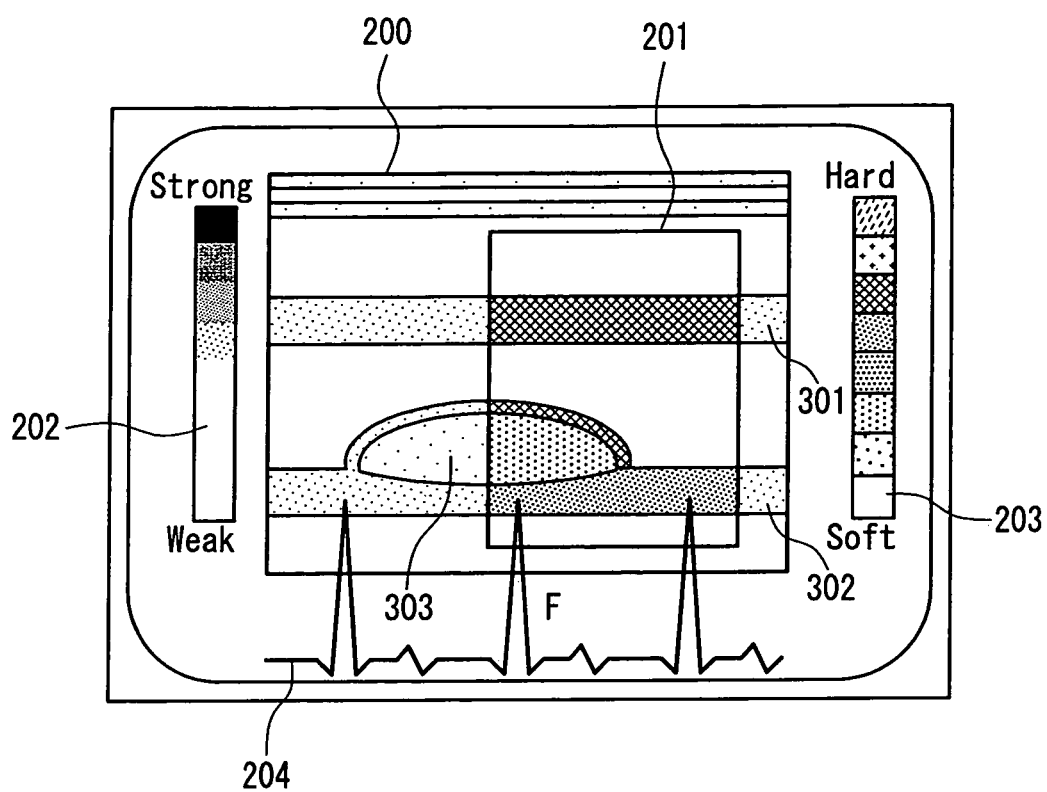
FIG. 3 is a view illustrating an exemplary display screen of a monitor 107 of the ultrasonic diagnostic apparatus.

FIG. 3 is a view illustrating an exemplary display screen of the monitor 107. On the monitor screen, a distribution image 201 of the elastic modulus is superimposed on a tomographic image 200. FIG. 3 shows the tomographic image 200 of a blood vessel with an atheroma 303 in a long axis direction (an anterior wall 301 and a posterior wall 302 of the blood vessel) by way of example. Further, a reflection intensity scale 202 indicating the correspondence between the reflection intensity of the tomographic image 200 and the luminance on the screen, an elastic modulus scale 203 indicating the correspondence between the elastic modulus and the color tone or luminance on the screen, an electrocardiographic or cardiac sound waveform 204, and the like are displayed.

In FIG. 2, the initializing signal to the tissue tracing unit 115 is selected by operating the switch 121. When a moving contact of the switch 121 selects a b-side contact, the initialization is performed by using the electrocardiographic waveform as in a conventional method. When the moving contact of the switch 121 selects an a-side contact, the initialization can be performed by the method of the present embodiment. Consequently, when there is a need to obtain distribution images of the elastic modulus of a plurality of subjects in a short time, the distribution images of the elastic modulus can be obtained promptly without requiring complicated operations such as reattaching an electrocardiograph by using the initialization method of the present embodiment. By setting the switch 121 to the other side, it is also possible to deal with the case where initialization is required to be performed reliably by using the electrocardiographic waveform.

Further, when the moving contact of the switch 121 selects a c-side contact, the initialization can be performed by using a property that is in synchronization with a heartbeat, the property being detected by the heartbeat information measurement unit 122 such as a pulsimeter, a real time sphygmomanometer, a sphygmograph, or the like provided outside the device. Since a pulsimeter, a real time sphygmomanometer, a sphygmograph, or the like can be connected between a subject and the device with fewer cables and attached to the subject easily as compared with an electrocardiograph, it is possible to save an operator a lot of time and labor.

Further, the input signal to the property detection unit 120 can be selected by operating the switch 119. When a moving contact of the switch 119 selects an a-side contact, the initializing pulse can be generated based on the tissue tracing waveform from the tissue tracing unit 115. When the moving contact of the switch 119 selects a b-side contact, the initializing pulse can be produced based on the velocity or the intensity of a blood flow in a blood vessel or the Doppler shift due to the movement of the tissue. Further, when the moving contact of the switch 119 selects a c-side contact, the initializing pulse can be produced based on the amplitude or the phase of the received signal or the like.

In the above-described example, the description relates to the ultrasonic diagnostic apparatus that calculates a strain of a tissue of a subject in accordance with a change in blood pressure in one heartbeat so as to obtain an elastic modulus. However, the present embodiment also can be applied to an ultrasonic diagnostic apparatus that traces a tissue of a subject in accordance with pressure relaxation or vibration produced externally, so as to obtain a tissue property of the subject such as a strain, an elastic modulus, a viscosity coefficient, or the like. In such a case, the initializing pulse to the tissue tracing unit is in synchronization with the external pressure relaxation or vibration.

(Embodiment 2)

Figure 4:
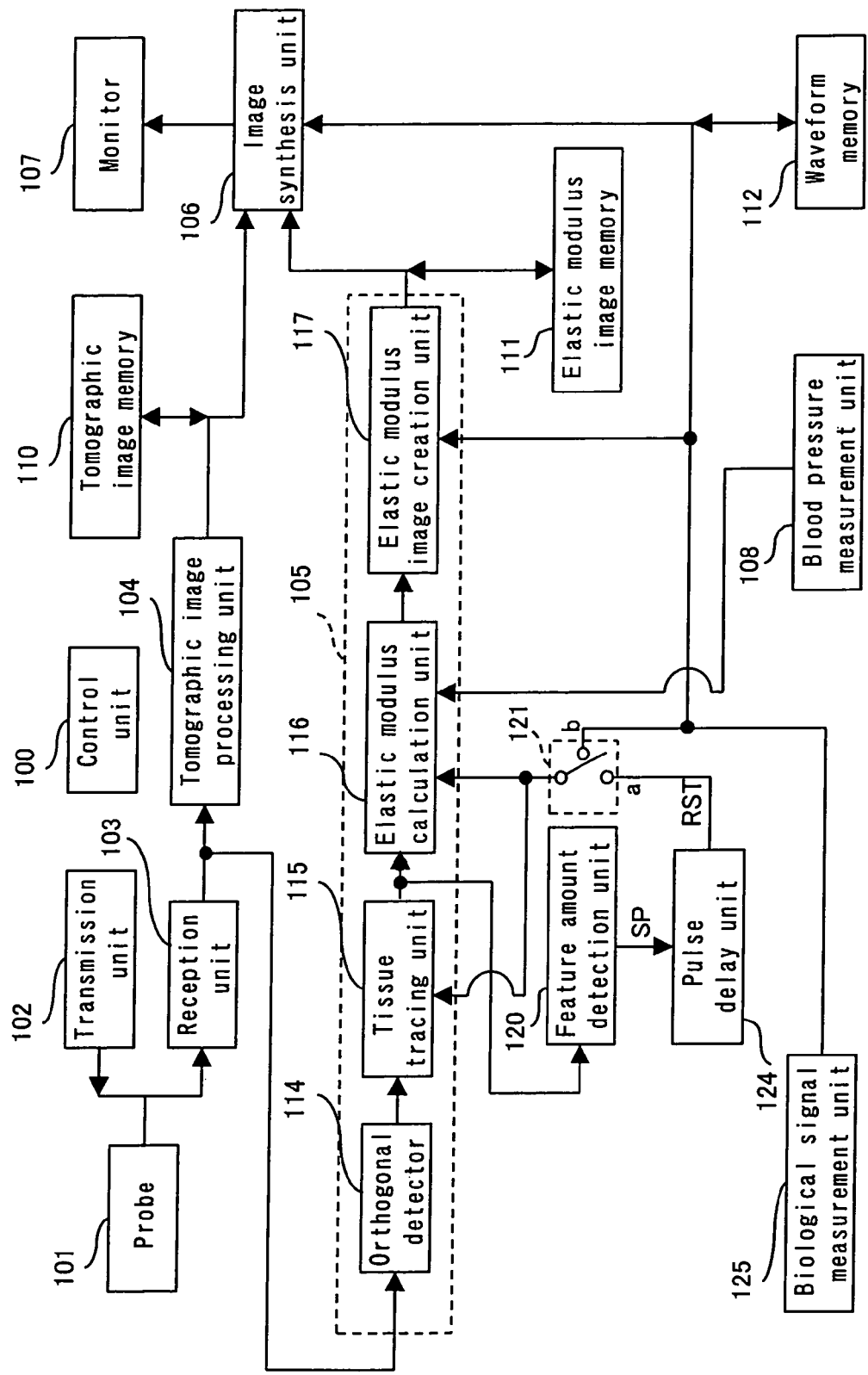
FIG. 4 is a block diagram showing an ultrasonic diagnostic apparatus according to Embodiment 2 of the present invention.

FIG. 4 is a block diagram showing an exemplary configuration of an ultrasonic diagnostic apparatus according to Embodiment 2 of the present invention. In FIG. 4, the same components as those shown in FIG. 2 with regard to Embodiment 1 are denoted with the same reference numerals, and descriptions thereof will be omitted.

A property detection unit 120, which is one of the central components for tracing the movement of a tissue of a subject with accuracy in the present embodiment, analyzes the amplitude or the phase of a one-dimensional received signal or a Doppler shift or a tissue tracing waveform obtained by analyzing the amplitude or the phase of the received signal, detects a property (including a heartbeat) concerning the movement of the subject, particularly a property that is in synchronization with the movement, and generates a synchronization pulse SP as a property detection signal from the timing of detecting the property. In the present embodiment, since the one-dimensional signal before an image is created is used, a signal that is in synchronization with a heartbeat can be detected easily and accurately as compared with a method in which a signal that is in synchronization with a heartbeat is detected by analyzing an image. A pulse delay unit 124 as another principal component delays the synchronization pulse for a predetermined delay time to generate an initializing pulse RST as an initializing signal for initializing a tissue tracing unit 115. The initializing pulse RST is also a timing signal for calculating an elastic modulus in an elastic modulus calculation unit 116.

A switch 121 selects the initializing signal to the tissue tracing unit 115 from the outputs of the pulse delay unit 124 and a biological signal measurement unit 125. The biological signal measurement unit 125 is means for measuring an electrocardiogram, a cardiac sound, or the like. An exemplary display screen of a monitor 107 is the same as that shown in FIG. 3.

Next, operations of the property detection unit 120 and the pulse delay unit 124 as principal components in the present embodiment will be described in further detail with reference to FIGS. 5 and 6. Hereinafter, a description is given of the case where in FIG. 4, a common contact of the switch 121 selects an a-side contact so that the property detection signal RST obtained by delaying by the pulse delay unit 124 is used as the initializing signal for initializing the tissue tracing unit 115, and the property detection unit 120 detects the property concerning the movement of the tissue of the subject based on the tracing waveform of the tissue of the subject.

Figure 5:
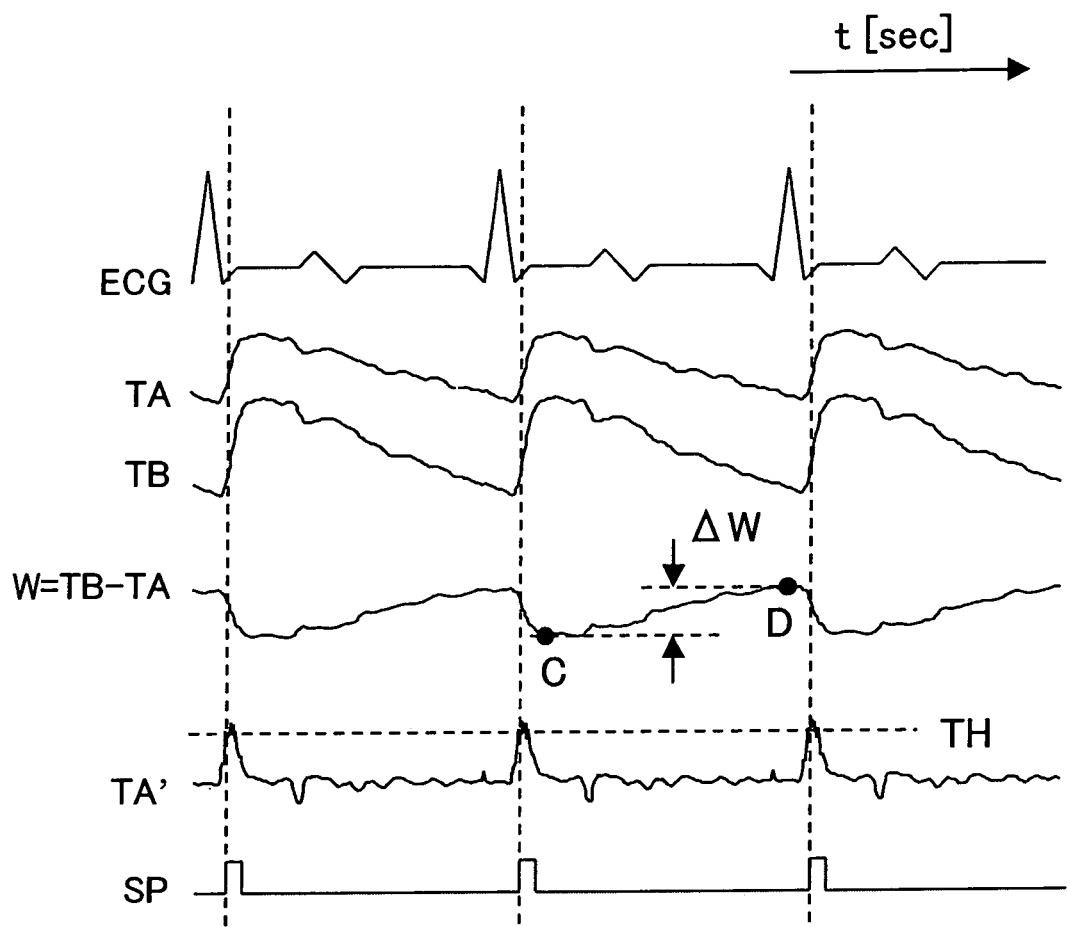
FIG. 5 is a waveform diagram for explaining an advantage of the ultrasonic diagnostic apparatus according to Embodiment 2.

FIG. 5 shows from the top an ECG waveform, a tracing waveform TA at a measurement point A of a blood vessel 300 (FIG. 22A), a tracing waveform TB at a measurement point B, a thickness change waveform W(=TB−TA), a differentiated waveform TA' of TA, and the synchronization pulse SP. Initially, the tracing waveform is processed so as to detect one synchronization pulse SP per one heartbeat. FIG. 5 shows an exemplary case where the differentiated waveform TA' of the tracing waveform TA is compared with a threshold value TH and the synchronization pulse SP is generated at the time when the differentiated waveform TA' exceeds the threshold value TH. However, the present embodiment is not limited thereto. Any information that moves in synchronization with a heartbeat is available such as a change in the amplitude or the phase of the received signal, the tissue tracing waveform itself, the thickness change waveform W, a change in the strain e, a pulse wave on a blood vessel, a blood flow velocity or a blood flow intensity detected by the Doppler shift of the received signal, a pulse, a momentary blood pressure waveform, a cardiac sound, differentiated waveforms thereof, and the like. In brief, it is important to generate one synchronization pulse SP per one heartbeat reliably.

By using the synchronization pulse SP, the tracing waveforms can be initialized once per one heartbeat without the need for a special connection of an electrocardiograph, a phonocardiograph, or the like between the subject and the device. In this case, the timing of the initialization falls within a period of blood vessel expansion. A blood vessel expands rapidly and contracts gradually. In order to obtain the elastic modulus, it is required to obtain a maximum value and a minimum value (a difference therebetween: ΔW) of a change in the thickness of a blood vessel wall. Although the minimum value appears at an end stage of the blood vessel expansion period, i.e., immediately after the initialization (point C in FIG. 5), the maximum value appears at an end stage of a blood vessel contraction period, i.e., after the elapse of a considerable time from the initialization (point D in FIG. 5).

Since the tissue of the subject is traced by adding a position change cumulatively as expressed by the equation (2) above, the tracing accuracy decreases with time from the initialization. Accordingly, considerable errors are accumulated at the point D where a considerable time has elapsed from the initialization. For this reason, in order to increase the tracing accuracy, the points C and D preferably come immediately after the initialization.

To this end, in the present embodiment, the tracing waveforms are initialized by using a pulse obtained by allowing the synchronization pulse SP to pass through the pulse delay unit 124 instead of using the synchronization pulse SP directly. More specifically, as shown in FIG. 6, the synchronization pulse SP is delayed for a time $\alpha T1$ that is proportional to an interval T1 between two synchronization pulses SP (a current pulse and an immediately preceding pulse), thereby generating the initializing pulse RST. The tracing waveforms are initialized by resetting the tissue tracing unit 115 using the initializing pulse RST thus obtained. The delay time may be set to approximately 90% of the interval between the two property detection pulses, i.e., synchronization pulses SP (the current pulse and the immediately preceding pulse), so that the timing of the initialization can be set immediately before an end stage of a blood vessel contraction period. Consequently, both the maximum value and the minimum value of the change in the thickness of the blood vessel wall are allowed to appear in a shorter time from the initialization (points B and C in FIG. 6). As a result, the tracing accuracy is prevented from decreasing, and the elastic modulus can be obtained with high tracing accuracy. Further, according to this method, the initialization can be performed at about the same timing as that of conventional initialization using an R wave of an electrocardiogram.

The heart does not always beat with the same period (particularly in the case of an irregular heartbeat). On this account, the delay time may be changed in accordance with the subject in a range of approximately 70% to 95% of the interval between the property detection pulses, set to 70% to 95% of an average value of immediately preceding several intervals between the property detection pulses, or set to 70% to 95% of a subsequent pulse interval that is estimated by approximating immediately processing several pulse intervals by a polynomial expression. Consequently, a heartbeat interval can be estimated more accurately, and the timing of the initialization can be set to fall at an end stage of a blood vessel contraction period accurately, which makes it possible to perform more appropriate initialization.

Figure 7:
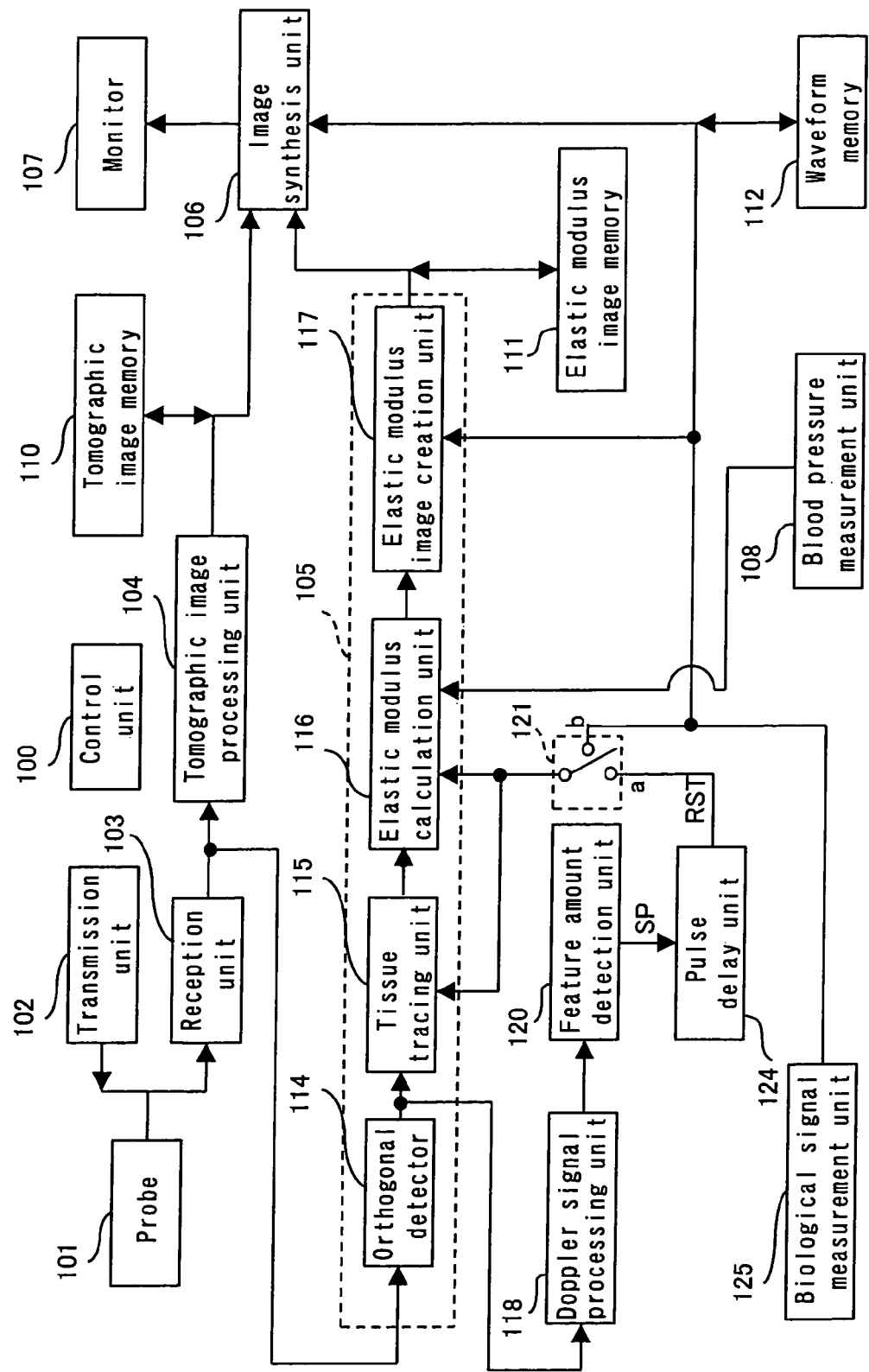
FIG. 7 is a block diagram showing an exemplary modification of the ultrasonic diagnostic apparatus according to Embodiment 2.
Figure 8:
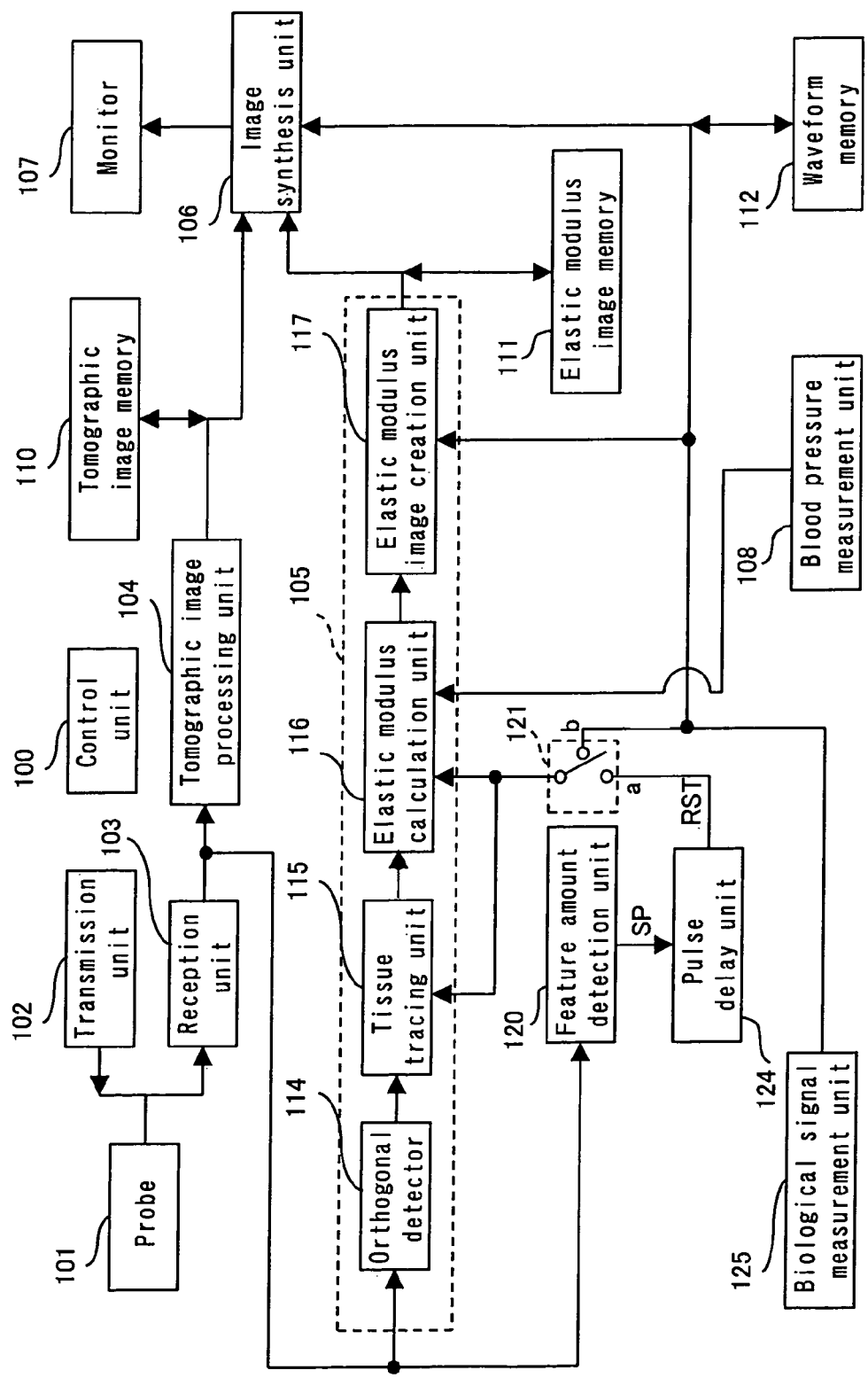
FIG. 8 is a block diagram showing another exemplary modification of the ultrasonic diagnostic apparatus according to Embodiment 2.

Further, as shown in FIG. 7, a Doppler signal processing unit 118 for detecting a Doppler shift of a received signal may be provided, so that a property concerning the movement is detected from the Doppler shift. The Doppler signal processing unit 118 also is provided in a conventional ultrasonic diagnostic apparatus to detect a blood flow. The velocity and the power of a blood flow reflect the movement of the heart directly. Thus, by using them, it is possible to generate one pulse per one heartbeat reliably with high accuracy. Further, as shown in FIG. 8, it is also possible to detect a property by analyzing a received signal directly. In such a case, the amplitude or the phase of a received signal from a certain depth is monitored, and a point at which the amplitude or the phase is changed significantly or the like is detected, whereby it is possible to generate one pulse per one heartbeat easily.

(Embodiment 3)

Figure 9:
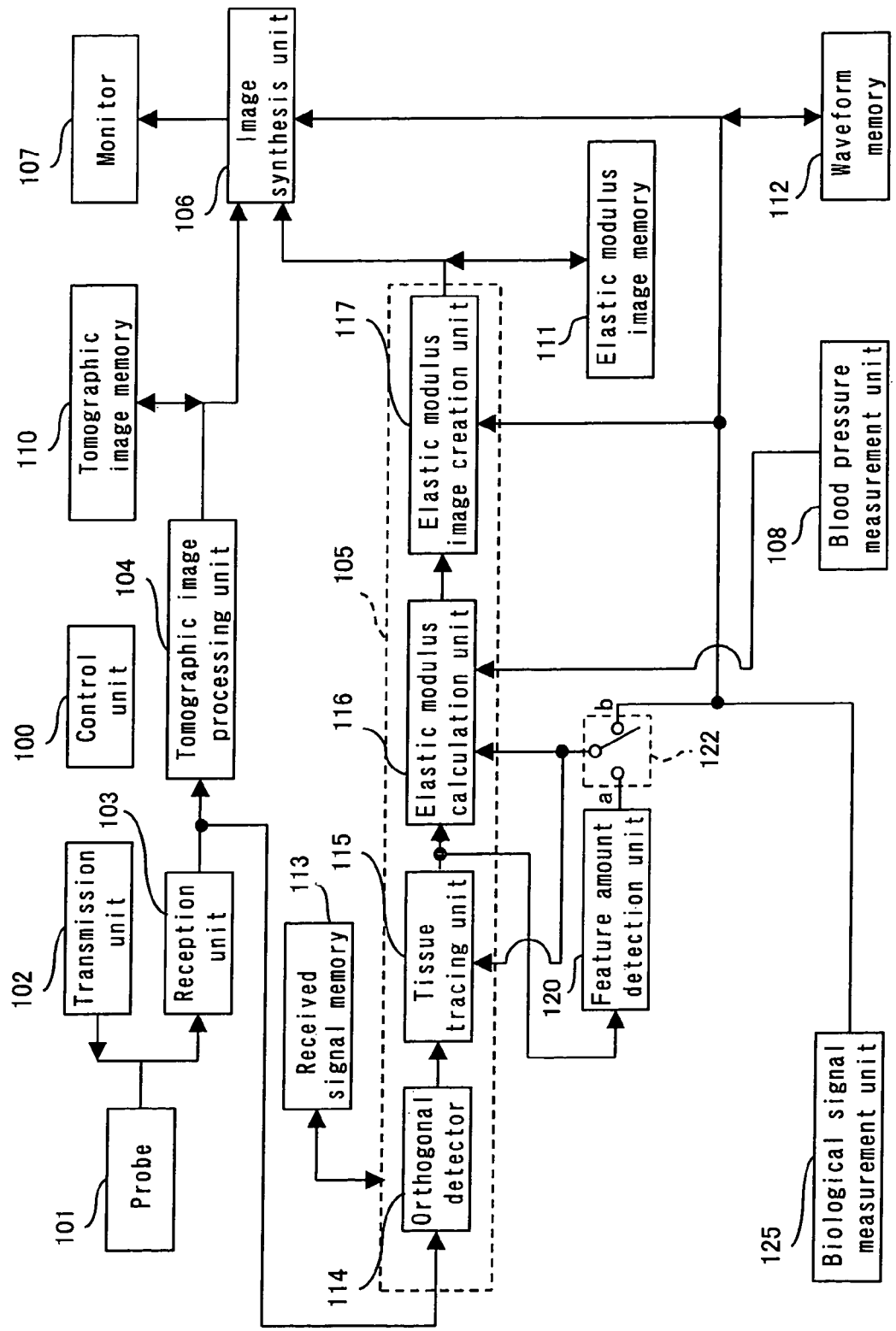
FIG. 9 is a block diagram showing an exemplary configuration of an ultrasonic diagnostic apparatus according to Embodiment 3 of the present invention.

FIG. 9 is a block diagram showing an exemplary configuration of an ultrasonic diagnostic apparatus according to Embodiment 3 of the present invention. The present embodiment is different from Embodiment 2 in that a received signal memory 113 is provided instead of the pulse delay unit 124 and a tracing waveform for obtaining an initializing pulse RST is provided separately from tracing waveforms for obtaining a thickness change. In FIG. 9, the components having the same configurations and functions as those in Embodiment 2 will be denoted with the same reference numerals, and descriptions thereof will be omitted.

In FIG. 9, the received signal memory 113 stores and reads/writes a received signal in the first-in first-out (FIFO) system, thereby providing the received signal with a predetermined delay time. The received signal may be one obtained either before or after quadrature demodulation.

Next, operations of a property detection unit 120 and the received signal memory 113 as principal components in the present embodiment will be described in detail with reference to FIGS. 10A and 10B. Hereinafter, a description is given of the case where a common contact of a switch 122 in FIG. 9 selects an a-side contact.

Figure 10A:
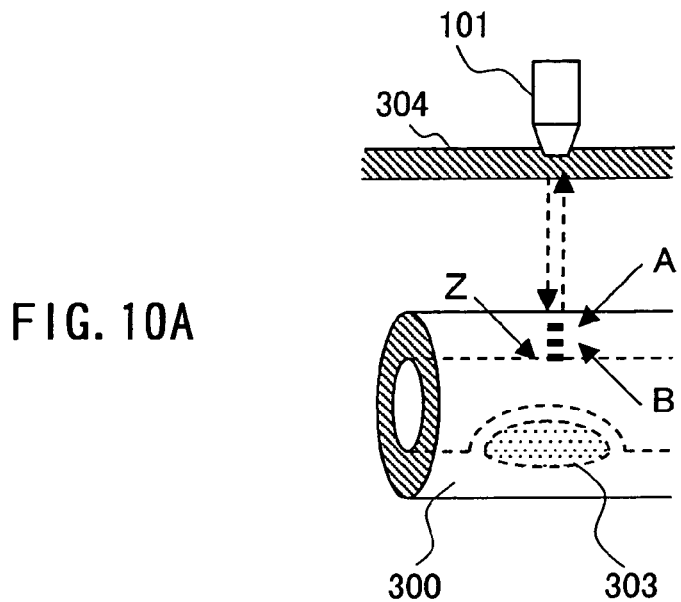
FIG. 10A is a schematic view showing places (measurement points) at which the movement of a tissue of a subject is traced by using the ultrasonic diagnostic apparatus according to Embodiment 3.
Figure 10B:
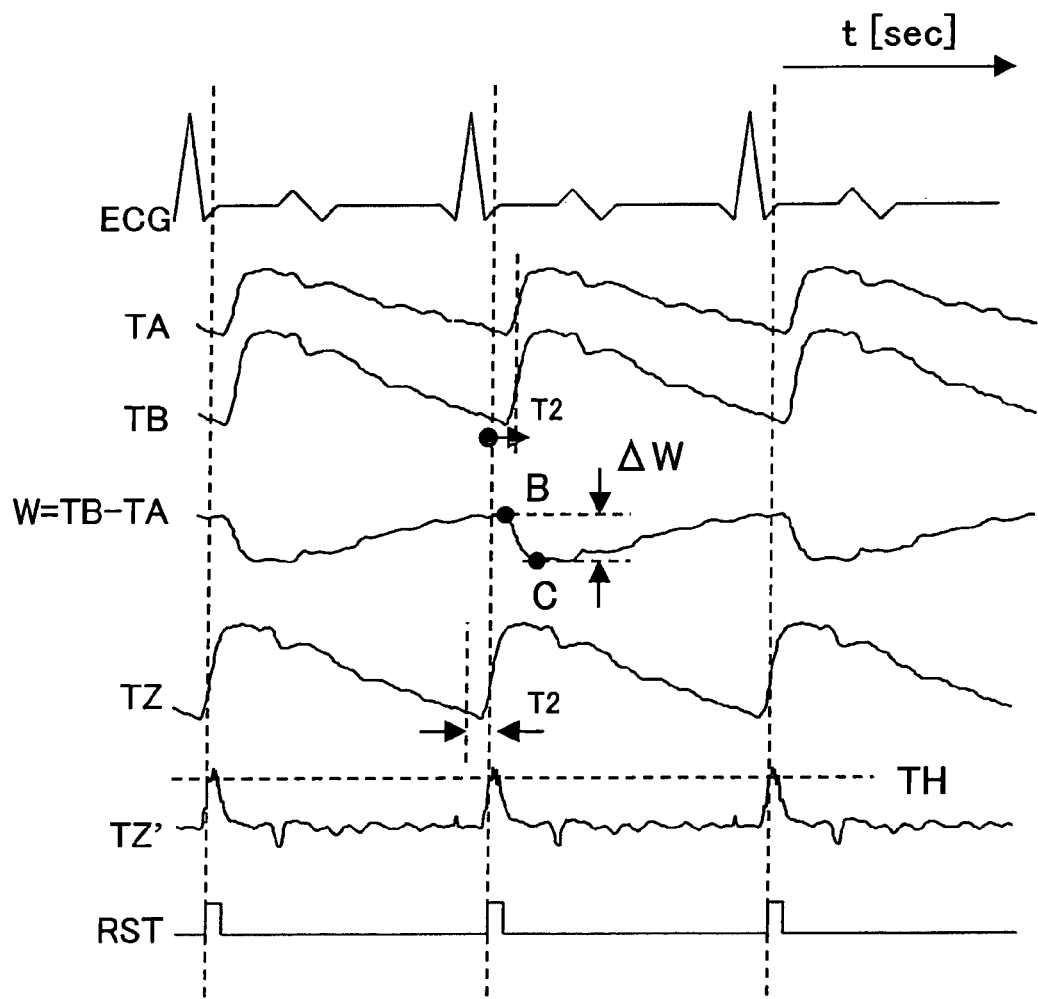
FIG. 10B is a waveform diagram for explaining an operation of the ultrasonic diagnostic apparatus according to Embodiment 3.

FIG. 10A is a schematic view showing places (measurement points) at which the movement of a tissue of a subject is traced, the figure containing a measurement point Z in addition to the measurement points A and B as shown in FIG. 22A. FIG. 10B shows from the top an ECG waveform, a tracing waveform TA at the measurement point A of a blood vessel 300 (FIG. 10A), a tracing waveform TB at the measurement point B, a thickness change waveform W (TB−TA), a tracing waveform TZ at the measurement point Z, a differentiated waveform TZ' of the tracing waveform TZ, and the initializing pulse RST. In the present embodiment, the tracing waveform is processed so as to detect one initializing pulse RST per one heartbeat. By using the initializing pulse RST, the tracing waveforms are initialized once per one heartbeat without the need for a special connection of an electrocardiograph, a phonocardiograph, or the like between the subject and the device. However, as described in Embodiment 2 with reference to FIG. 5, the timing of initialization falls within a blood vessel expansion period, and it takes a considerable time from the initialization until a maximum value of the thickness change waveform appears.

To solve this problem, in the present embodiment, the tracing waveform TZ for obtaining the initializing pulse RST and the tracing waveforms TA and TB for obtaining a thickness change are provided separately. The tracing waveform TZ for obtaining the initializing pulse is measured immediately after reception and subjected to processing for detecting a property concerning the movement, whereby the initializing pulse RST is created. The tracing waveforms TA and TB for obtaining a thickness change are stored initially in the received signal memory 113 and then transmitted to a tissue tracing unit 115 after a predetermined delay time, whereby the thickness change is obtained.

In order to achieve a sufficient effect and simplify the processing, the predetermined delay time is preferably a time T2 between immediately before an end stage of a blood vessel contraction period and the detection of the initializing pulse RST, which is obtained by analyzing the tracing waveform TZ, but may be a fixed value of approximately 0.1 to 0.2 seconds. Consequently, the timing of the initialization can be set immediately before the end stage of the blood vessel contraction period, and both the maximum value and a minimum value of the change in the thickness of a blood vessel wall are allowed to appear in a shorter time from the initialization (points B and C in FIG. 6). As a result, the elastic modulus can be obtained with high tracing accuracy.

There occurs a problem that an obtained distribution image of the elastic modulus and a tomographic image are out of time phase with each other since the elastic modulus is obtained from the tissue tracing waveforms that are obtained from the delayed received signals. However, in the present embodiment, a tomographic image memory 110 is provided so as to delay the tomographic image, thereby eliminating this problem.

Figure 11:
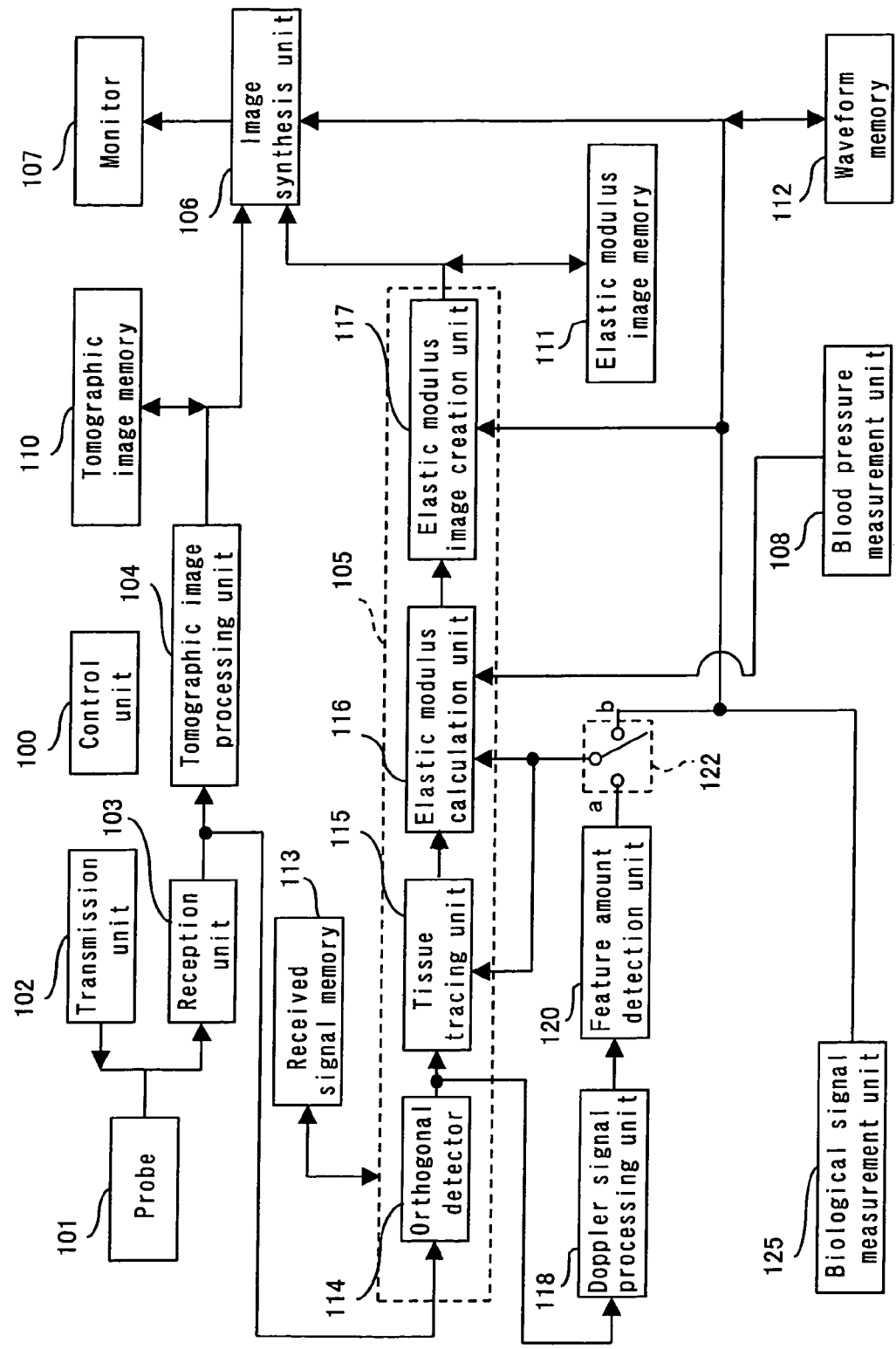
FIG. 11 is a block diagram showing an exemplary modification of the ultrasonic diagnostic apparatus according to Embodiment 3.
Figure 12:
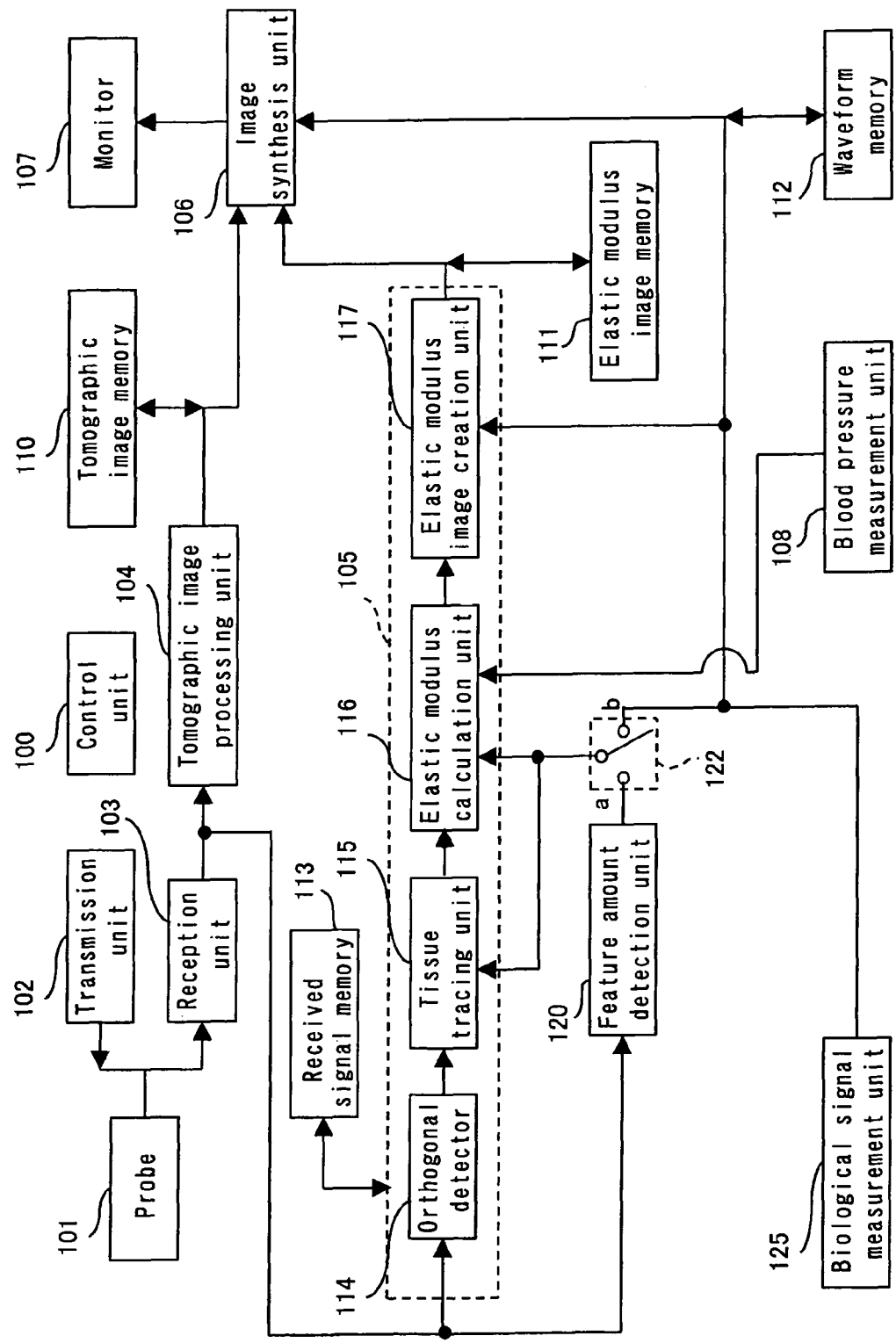
FIG. 12 is a block diagram showing another exemplary modification of the ultrasonic diagnostic apparatus according to Embodiment 3.

Further, as shown in FIG. 11, a Doppler signal processing unit 118 for detecting a Doppler shift of a received signal may be provided, so that a property concerning the movement is detected from the Doppler shift. The Doppler signal processing unit 118 also is provided in a conventional ultrasonic diagnostic apparatus to detect a blood flow. The velocity and the power of a blood flow reflect the movement of the heart directly. Thus, by using them, it is possible to generate one pulse per one heartbeat reliably with high accuracy. Further, as shown in FIG. 12, it is also possible to detect a property by analyzing a received signal directly. In such a case, the amplitude or the phase of a received signal from a certain depth is monitored, and a point at which the amplitude or the phase is changed significantly or the like is detected, whereby it is possible to generate one pulse per one heartbeat easily.

In the configuration in each of FIGS. 4 and 9, when the common contact of each of the switches 121 and 122 selects a b-side contact, the initialization is performed by using the electrocardiographic waveform or a cardiac sound waveform as in a conventional method. When the common contact of each of the switches 121 and 122 selects the a-side contact, the initialization can be performed by the method shown in each of the present embodiments. Consequently, in the case of a medical examination or the like where there is a need to obtain distribution images of the elastic modulus of a plurality of subjects in a short time, it is possible to obtain the distribution images of the elastic modulus promptly without requiring complicated operations such as reattaching an electrocardiograph or the like by using the method shown in each of the present embodiments. By setting each of the switches 121 and 122 to the other side, it is also possible to deal with the case where initialization is required to be performed reliably by using the electrocardiographic waveform or the like.

In each of Embodiments 2 and 3, the description relates to the ultrasonic diagnostic apparatus that calculates a strain of a tissue of a subject in accordance with a change in blood pressure in one heartbeat so as to obtain an elastic modulus. However, these embodiments also can be applied to an ultrasonic diagnostic apparatus that traces a tissue of a subject in accordance with pressure relaxation or vibration produced externally, so as to obtain a tissue property indicating a physical property of the tissue of the subject such as a strain, an elastic modulus, a viscosity coefficient, or the like. In such a case, it is important that the synchronization pulse to the tissue tracing unit is in synchronization with the external pressure relaxation or vibration, and that the predetermined delay time is adjusted in a range of 0% to 100% of the interval between the property detection pulses in accordance with the external pressure relaxation or vibration so that the maximum value and the minimum value of the thickness change width appear in as short a time from initialization as possible.

(Embodiment 4)

Figure 13:
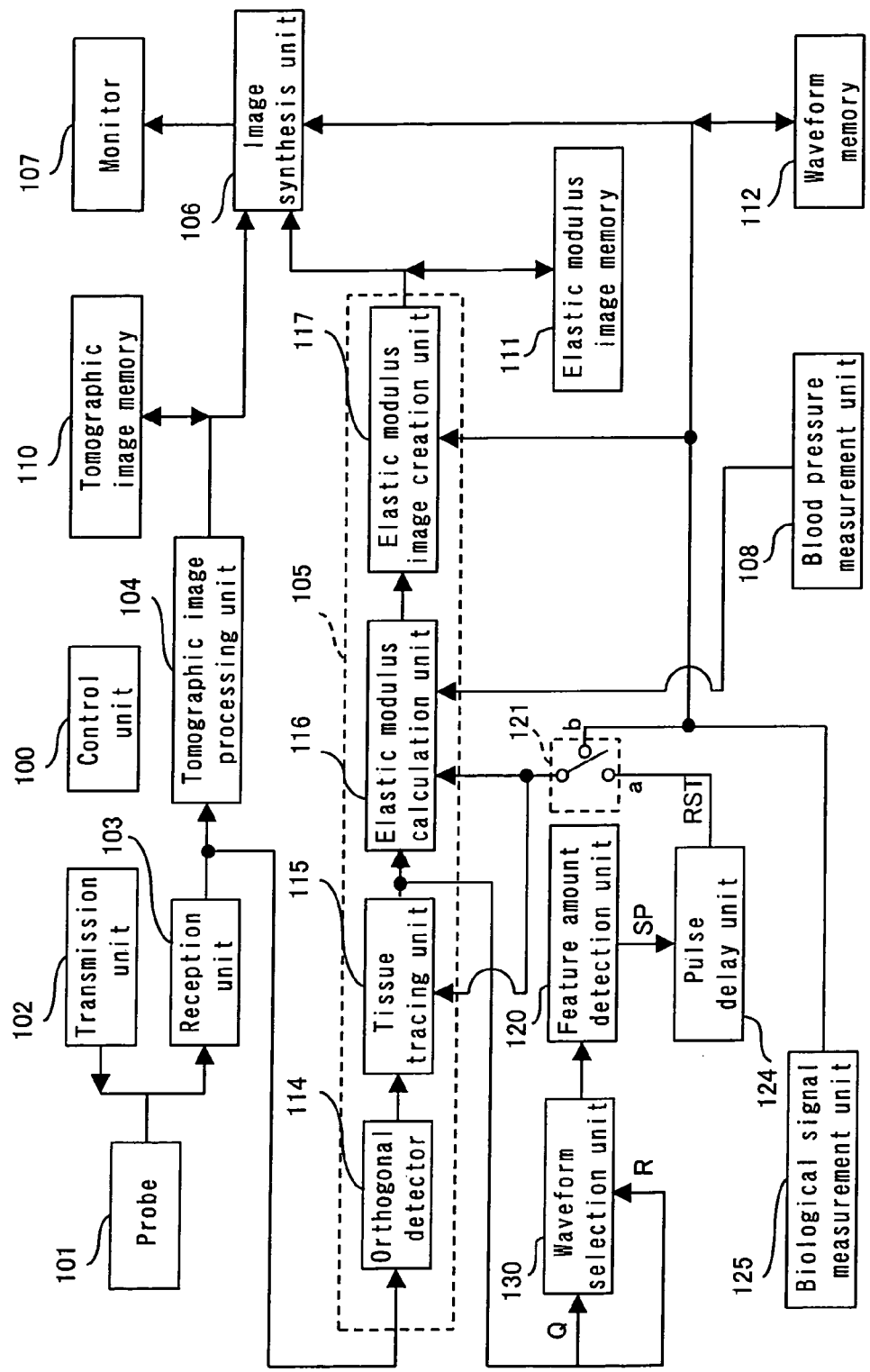
FIG. 13 is a block diagram showing an ultrasonic diagnostic apparatus according to Embodiment 4 of the present invention.

FIG. 13 is a block diagram showing an exemplary configuration of an ultrasonic diagnostic apparatus according to Embodiment 4 of the present invention. The ultrasonic diagnostic apparatus has a different configuration from that shown in FIG. 4 with regard to Embodiment 2 in that a waveform selection unit 130 is provided further. In FIG. 13, the components having the same configurations and functions as those in Embodiment 2 will be denoted with the same reference numerals, and descriptions thereof will be omitted.

The waveform selection unit 130 has two input terminals (input terminals R and Q), and analyzes waveforms input to the input terminal R and selects and outputs one from waveforms input to the input terminal Q based on the analysis result. In the configuration in FIG. 13, a plurality of tracing waveform signals are input to the input terminal Q of the waveform selection unit 130, and the plurality of tracing waveform signals are input to the input terminal R. The waveform selection unit 130 analyzes the tracing waveform signals input to the input terminal R, and selects one tracing waveform signal from the tracing waveform signals input to the input terminal Q using the analysis result.

Figure 6:
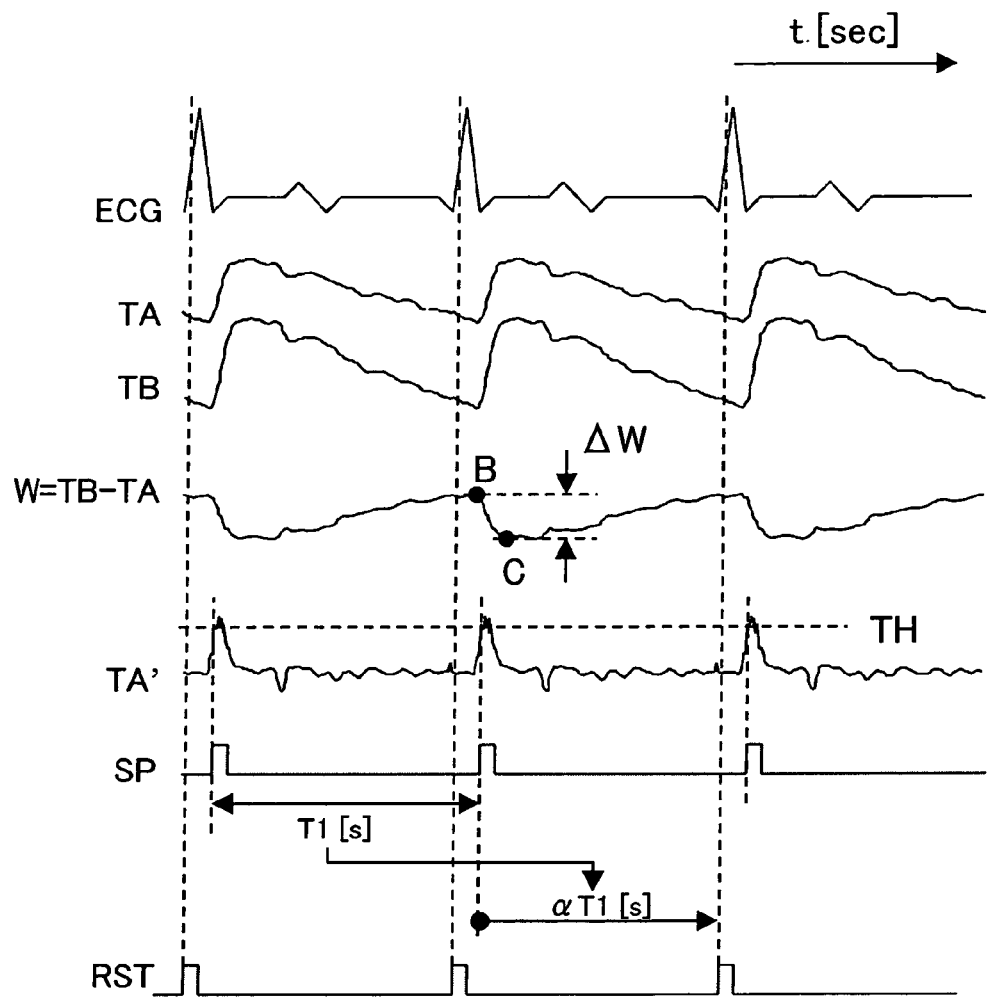
FIG. 6 is a waveform diagram for explaining an operation of the ultrasonic diagnostic apparatus according to Embodiment 2.

A property detection unit 120 analyzes the selected tracing waveform in the same manner as shown in FIG. 6, for example. That is, for example, the property detection unit 120 subjects a change in a tracing waveform TA at a measurement point A of a subject, i.e., a differentiated waveform thereof, to threshold processing, and generates one initializing pulse RST per one heartbeat, so that tracing waveforms in entire regions are initialized by the initializing pulse RST. The point of the present embodiment is how to select a measurement point of a tracing waveform for generating an initializing pulse.

Figure 14:
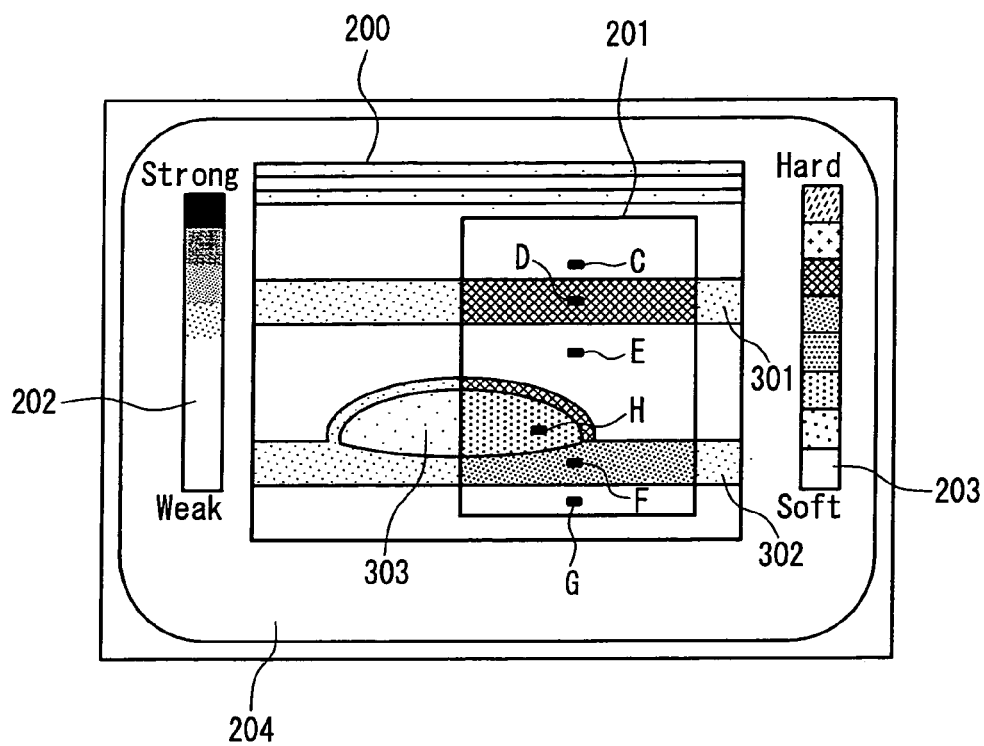
FIG. 14 is a view illustrating a screen of the ultrasonic diagnostic apparatus according to Embodiment 4.
Figure 15:
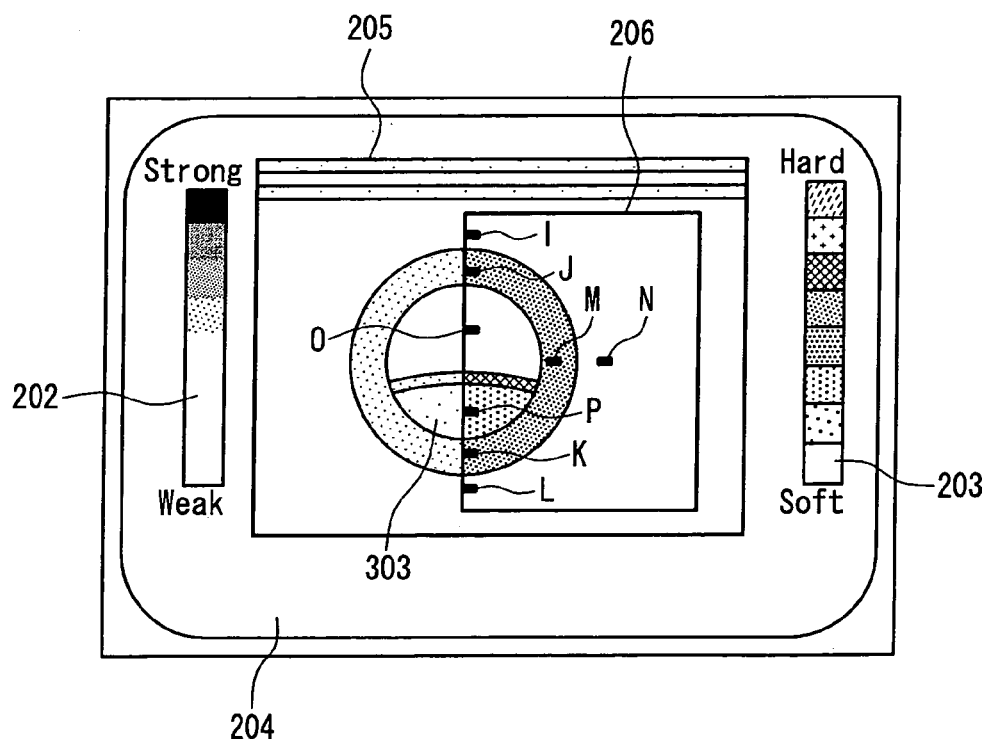
FIG. 15 is a view illustrating another screen of the ultrasonic diagnostic apparatus according to Embodiment 4.
Figure 16A:
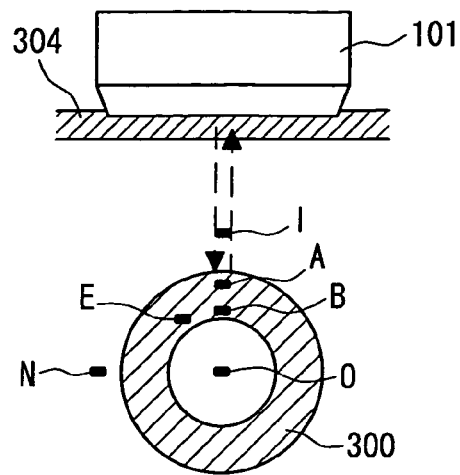
FIG. 16A shows respective measurement points of a subject.
Figure 16B:
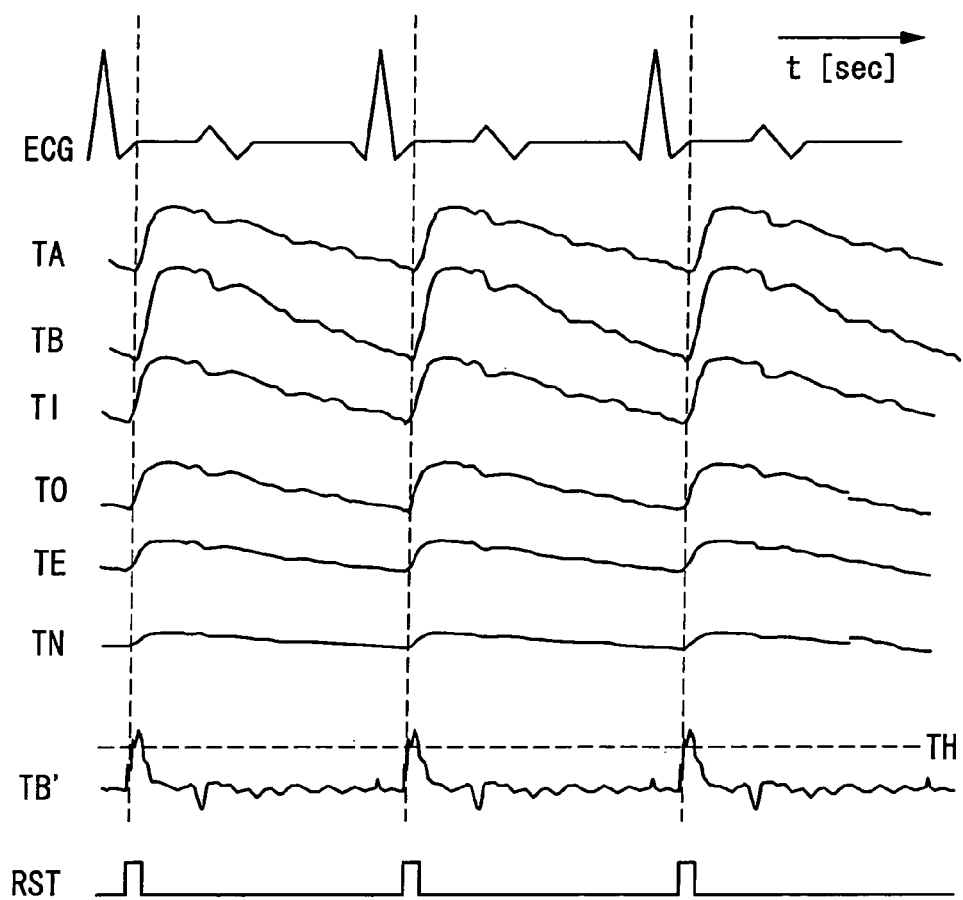
FIG. 16B is a waveform diagram showing exemplary tracing waveforms obtained from the respective measurement points shown in FIG. 16A.

Hereinafter, an operation of the ultrasonic diagnostic apparatus according to the present embodiment will be described more specifically. FIGS. 14 and 15 illustrate exemplary display screens of a monitor 107. In FIG. 14, a tomographic image 200 of a blood vessel with an atheroma 303 in a long axis direction and a distribution image 201 of an elastic modulus for the corresponding position are displayed such that the distribution image 201 of the elastic modulus is superimposed on the tomographic image 200. In FIG. 15, a tomographic image 205 of the blood vessel with the atheroma 303 in a short axis direction and a distribution image 206 of an elastic modulus for the corresponding position are displayed such that the distribution image 206 of the elastic modulus is superimposed on the tomographic image 205. In FIGS. 14 and 15, C to P denote measurement points of tracing waveforms. FIG. 16B shows exemplary tracing waveforms obtained at respective measurement points shown in FIG. 16A. As shown in FIG. 16B, the amplitudes and S/N ratios of the tracing waveforms differ greatly from each other due to a difference between a traveling direction of an ultrasonic wave and a movement direction of a tissue of a subject or a difference in the reflectance of the tissue. Thus, in order to generate an initializing pulse with accuracy, it is important how a measurement point of the tracing waveform is selected.

As shown in FIG. 14, in the image of a cross section of the blood vessel in the long axis direction, a measurement point D or F is most suitable, and a measurement point C or G is suitable. Since the measurement point D or F is located on a blood vessel wall, a good S/N ratio is obtained due to a large amplitude of an ultrasonic echo, and accordingly an accurate tracing waveform can be obtained, which also is ascribed to the fact that pulsation of the blood vessel caused by blood pressure is reflected directly at this point. Although it is possible to obtain an accurate tracing waveform also at the measurement point C or G similarly, the amplitude of pulsation is slightly smaller due to the distance from the blood vessel. A measurement point E is unsuitable since it is located inside the blood vessel. Accordingly, an S/N ratio is unfavorable due to a small amplitude of the ultrasonic echo, and it is impossible to obtain an accurate tracing waveform. Further, a measurement point H is unsuitable since it is located inside the atheroma, where a movement direction of the tissue is not necessarily in parallel with a traveling direction of the ultrasonic wave. Accordingly, it is considered impossible to obtain an accurate tracing waveform.

As shown in FIG. 15, in the image of a cross section of the blood vessel in the short axis direction, a measurement point J or K is most suitable, and a measurement point I or L is suitable. Since the measurement point J or K is located on the blood vessel wall, a good S/N ratio is obtained due to a large amplitude of an ultrasonic echo, and accordingly an accurate tracing waveform can be obtained, which also is ascribed to the fact that pulsation of the blood vessel caused by blood pressure is reflected directly at this point. Although it is possible to obtain an accurate tracing waveform also at the measurement point I or L similarly, the amplitude of pulsation is slightly smaller due to the distance from the blood vessel. A measurement point O is unsuitable since it is located inside the blood vessel. Accordingly, an S/N ratio is unfavorable due to a small amplitude of the ultrasonic echo, and it is impossible to obtain an accurate tracing waveform. Further, a measurement point P is unsuitable since it is located inside the atheroma, where a movement direction of the tissue is not necessarily in parallel with a traveling direction of the ultrasonic wave. Accordingly, it is considered impossible to obtain an accurate tracing waveform. Although a measurement point M is located on the blood vessel wall, accurate tracing is impossible because of the fact that a direction of pulsation is horizontal, whereas the traveling direction of the ultrasonic wave is vertical at this point. Therefore, the measurement point M is unsuitable. A measurement point N is also unsuitable for similar reasons.

In the ultrasonic diagnostic apparatus having the configuration shown in FIG. 13, the waveform selection unit 130 selects one tracing waveform from the plurality of tracing waveform signals input to the input terminal Q using the result of analyzing the plurality of tracing waveform signals input to the input terminal R. The tracing waveform selected by the waveform selection unit 130 is input to the property detection unit 120. The property detection unit 120 analyzes a tracing waveform at the corresponding position and generates a synchronization pulse SP. A pulse delay unit 124 delays the synchronization pulse SP to generate an initializing pulse RST. In this manner, a tracing waveform most suitable for generating the initializing pulse RST can be selected automatically. The most suitable tracing waveform can be selected as follows.

For example, the most suitable tracing waveform can be selected by using characteristics that a tracing waveform at the most suitable measurement point has a large amplitude, a low noise level, and periodicity. An amount of noise may be determined as follows. That is, tracing waveforms for several periods are compared so as to evaluate variations in the waveforms, or a tracing waveform that has passed through a low-pass filter is compared with an original tracing waveform. The periodicity may be determined by obtaining a period using a correlation function or the like. It is also effective to use a frequency domain in an FFT or the like for the periodicity determination. Further, based on the fact that the movement on a tracing waveform is different between a blood flow part and a blood vessel wall part, the blood vessel wall part may be determined by obtaining a boundary between the blood vessel wall and the blood flow part. The most suitable tracing waveform is selected in the above-mentioned manner, and the property detection unit 120 and the like are operated as in the above-described embodiments, whereby it is possible to trace a tissue of a subject more accurately with a simple operation of only applying a probe to the subject without the need for a special connection of an electrocardiograph or the like between the subject and the device.

Figure 17:
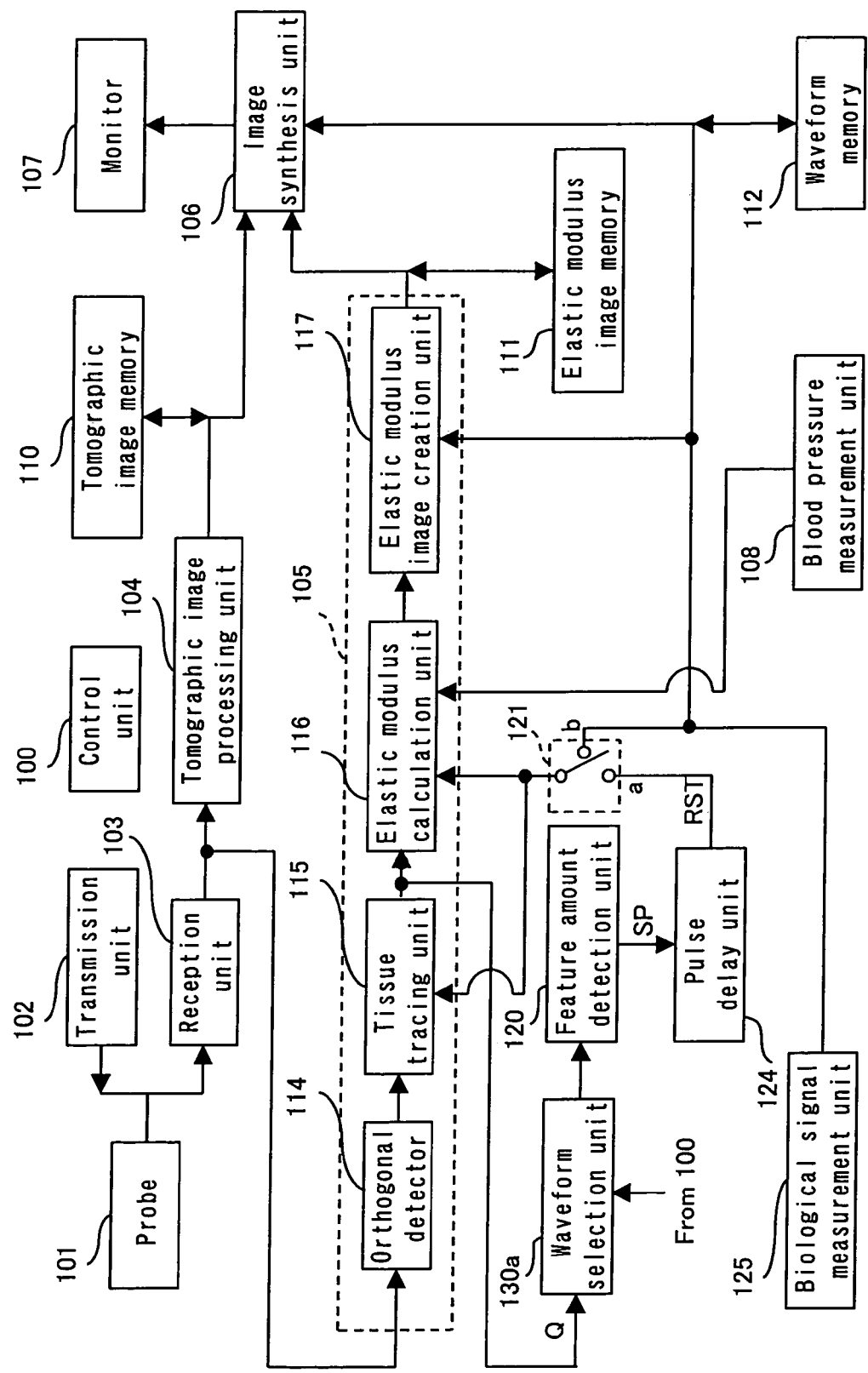
FIG. 17 is a block diagram showing an exemplary modification of the ultrasonic diagnostic apparatus according to Embodiment 4 of the present invention.

FIG. 17 shows another configuration of the ultrasonic diagnostic apparatus regarding how to select a measurement point of a tracing waveform. In this configuration, a plurality of tracing waveform signals are input to an input terminal Q of a waveform selection unit 130a. Further, a user specifies the most suitable measurement point via a control unit 100. The control unit 100 provides the waveform selection unit 130a with information on the specified position, and the waveform selection unit 130a selects the corresponding tracing waveform and inputs the same to a property detection unit 120. The property detection unit 120 analyzes a tracing waveform at the corresponding position and generates a synchronization pulse SP, and a pulse delay unit 124 generates an initializing pulse RST. According to this configuration, it is possible to deal with the case where it is difficult to determine a measurement point automatically due to a deformed blood vessel or the like.

Figure 18:
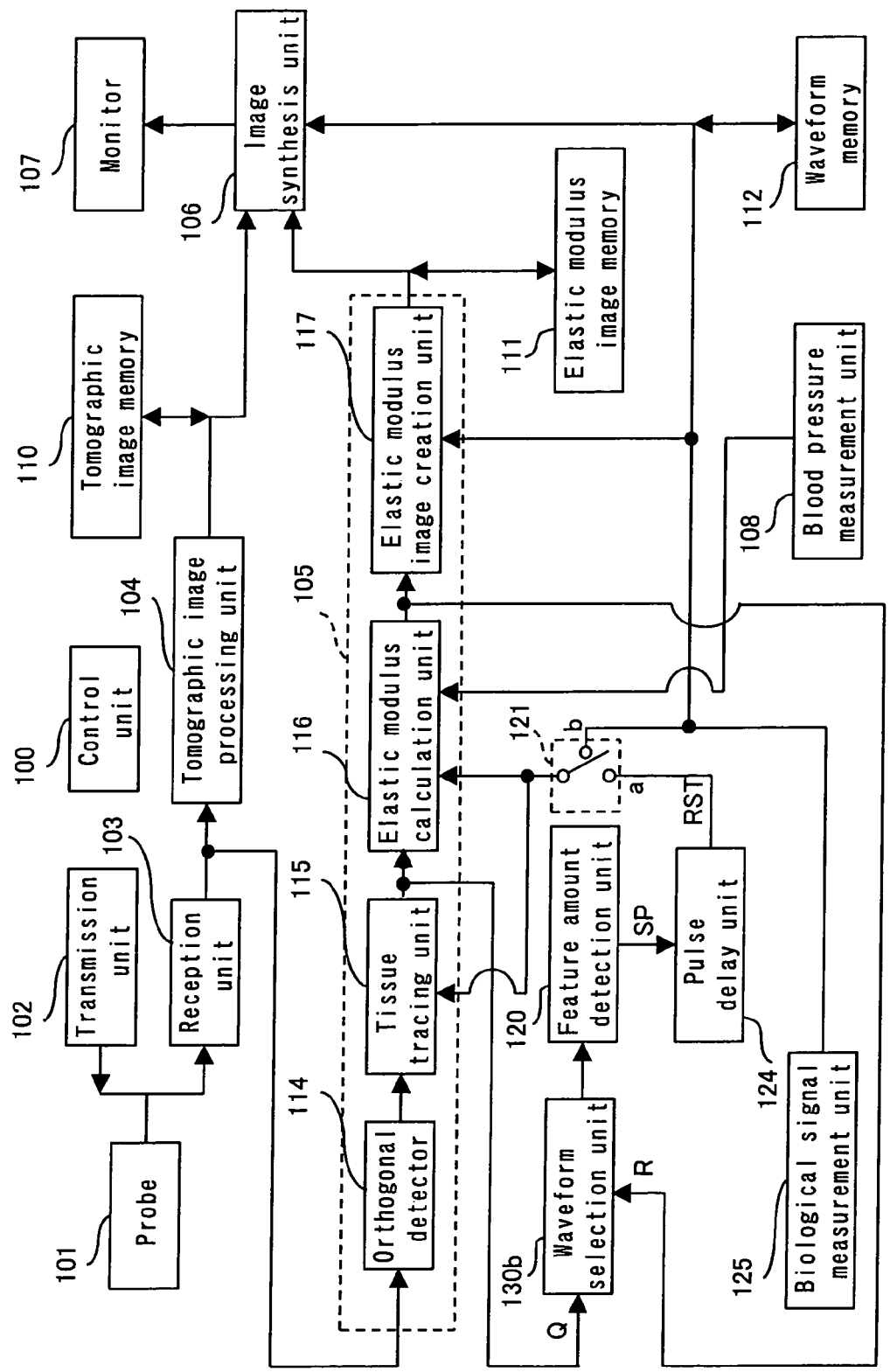
FIG. 18 is a block diagram showing another exemplary modification of the ultrasonic diagnostic apparatus according to Embodiment 4.

FIG. 18 shows still another configuration of the ultrasonic diagnostic apparatus. In this configuration, a local elastic modulus as an output of an elastic modulus calculation unit 116 is input to an input terminal R of a waveform selection unit 130b. The waveform selection unit 130b detects a blood vessel wall that extends in parallel with an ultrasonic beam from the local elastic modulus, selects based on the detected blood vessel wall a tracing waveform at that position from a plurality of tracing waveform signals Q, and inputs the same to a property detection unit 120. The property detection unit 120 analyzes the selected tracing waveform and generates an initializing pulse RST as described above. Since the local elastic modulus is obviously different between a blood vessel part and a blood flow part, a distinction therebetween is possible. In the above-mentioned manner, it is possible to trace a tissue of a subject more accurately with a simple operation of only applying a probe to the subject.

Figure 19:
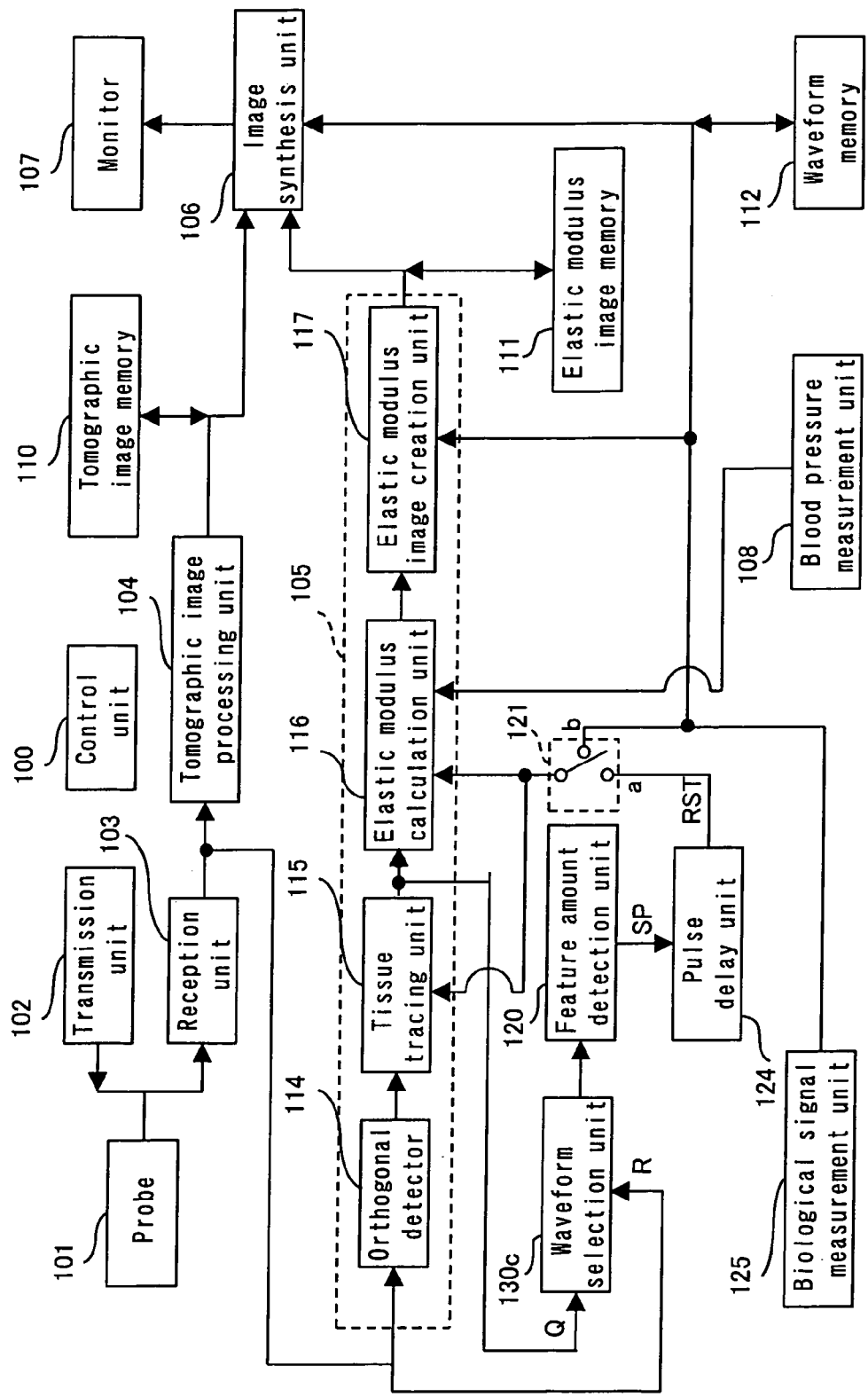
FIG. 19 is a block diagram showing still another exemplary modification of the ultrasonic diagnostic apparatus according to Embodiment 4.

FIG. 19 shows still another configuration of the ultrasonic diagnostic apparatus. In this configuration, a received signal from a reception unit 103 is input to an input terminal R of a waveform selection unit 130c. The waveform selection unit 130c analyzes the amplitude of the received signal so as to detect a boundary between a blood flow and a blood vessel wall. Then, as in the configuration in FIG. 18, a property detection unit 120 analyzes a tracing waveform at the position on a blood vessel wall side, and generates an initializing pulse RST. Since the intensity of the received signal is high on the blood vessel wall and low in the blood flow part, a distinction therebetween is possible.

Figure 20:
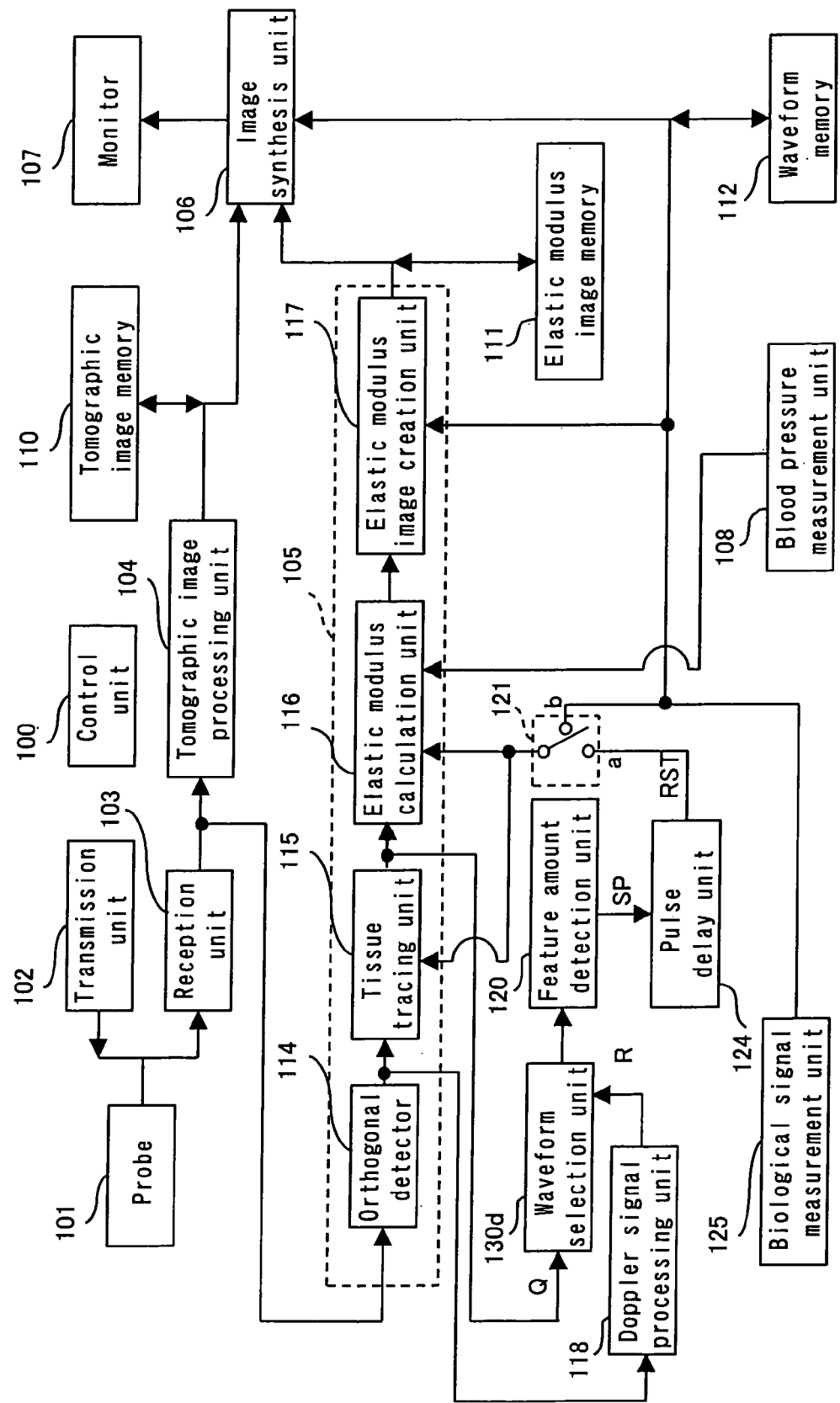
FIG. 20 is a block diagram showing still another exemplary modification of the ultrasonic diagnostic apparatus according to Embodiment 4.
Figure 21:
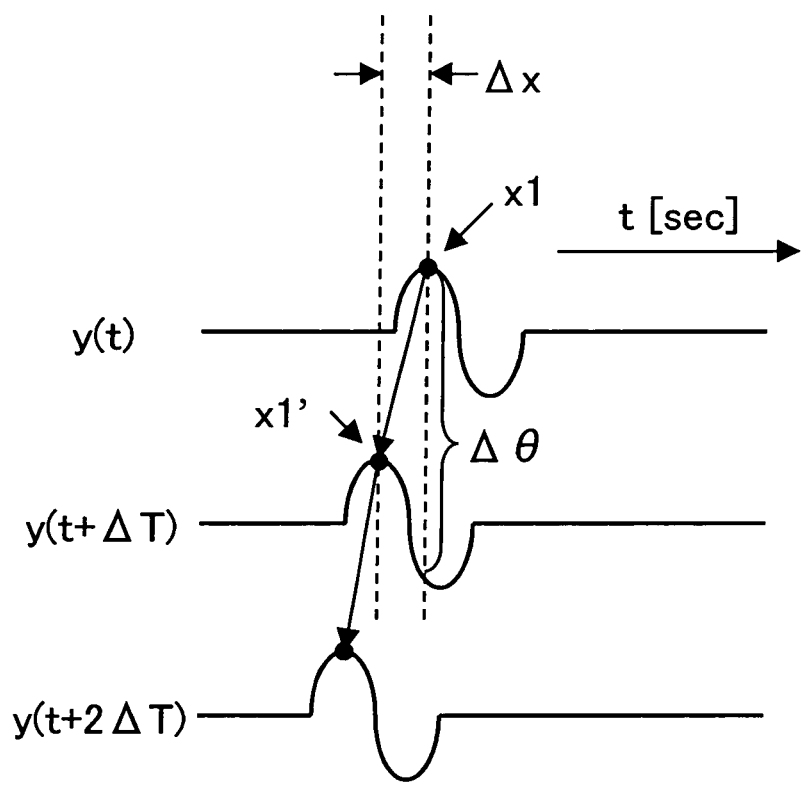
FIG. 21 is a waveform diagram for explaining a method of tracing a tissue of a subject according to a conventional example.

FIG. 20 shows still another configuration of the ultrasonic diagnostic apparatus. In this configuration, a Doppler signal processing unit 118 is provided, which analyzes a Doppler shift of a received signal, detects a blood flow, and supplies an input terminal R of a waveform selection unit 130d with that data. The waveform selection unit 130d estimates a blood vessel wall existing outside the detected blood flow. Then, as in the configuration in FIG. 18, a property detection unit 120 analyzes a tracing waveform at the position on a blood vessel wall side, and generates an initializing pulse RST.

In each of the above-mentioned configurations, signals to be input to the input terminal Q of the waveform selection unit 130 are not limited to the plurality of tracing waveform signals. For example, the Doppler shift signal or the received signal as shown in FIG. 7 or 8 is also available.

In the above, the description relates to the ultrasonic diagnostic apparatus that calculates a strain of a tissue of a subject in accordance with a change in blood pressure in one heartbeat so as to obtain an elastic modulus. However, the present embodiment also can be applied to an ultrasonic diagnostic apparatus that traces a tissue of a subject in accordance with pressure relaxation or vibration produced externally, so as to obtain a tissue property of the subject such as a strain, an elastic modulus, a viscosity coefficient, or the like. In such a case, the synchronization pulse to the tissue tracing unit is in synchronization with the external pressure relaxation or vibration.

Further, the present invention is not limited to the ultrasonic diagnostic apparatus whose final output is an elastic modulus, but also can be applied to an ultrasonic diagnostic apparatus for detecting a cancerous or tumorous tissue by obtaining a tissue tracing waveform and measuring a strain, an elastic modulus, or a viscosity coefficient, or an ultrasonic diagnostic apparatus for detecting arteriosclerosis from an Intima-Media Thickness (IMT) of a blood vessel, a change in the internal diameter of a blood vessel, a stiffness parameter, a pulse wave velocity, or the like.

Industrial Applicability

The ultrasonic diagnostic apparatus according to the present invention is capable of tracing the movement of a tissue of a subject with accuracy with a simple operation of only applying a probe to the subject without the necessity for a special connection of an electrocardiograph or the like between the subject and the device. Therefore, it is possible to obtain easily a tissue property such as an elastic modulus, a strain or a strain rate, a viscosity coefficient, or the like. The ultrasonic diagnostic apparatus according to the present invention saves an operator time and labor and is useful in a medical application and the like.

The invention claimed is:
1. An ultrasonic diagnostic apparatus, comprising:
   an ultrasonic wave transmitter that transmits an ultrasonic wave to a subject;

an ultrasonic wave receiver that receives the ultrasonic wave from the subject and outputs a received signal based upon the received ultrasonic wave;
a tissue tracing unit that generates a tissue tracing waveform by analyzing the received signal supplied from the ultrasonic wave receiver, said tissue tracing waveform including a waveform that traces a position of a tissue of the subject; and
a detection unit that detects initialization timings by analyzing a change to an aspect of the tissue tracing waveform without using information from an electrocardiograph, and outputs initializing pulses corresponding to the initialization timings
wherein said tissue tracing unit is repeatedly initialized based on the initialization pulses.

2. The ultrasonic diagnostic apparatus according to claim 1, further comprising a selection unit that analyzes tissue tracing waveforms of a plurality of tissues of the subject to select one from the plurality of tissues of the subject,
wherein the detection unit detects the initialization timings by analyzing the tissue tracing waveform of the selected tissue of the subject, and outputs the initializing pulses corresponding to the initialization timings.

3. The ultrasonic diagnostic apparatus according to claim 1, further comprising a selection unit which analyzes a plurality of received signals to select one from a plurality of tissues of the subject,
wherein the detection unit detects the initialization timings by analyzing the tissue tracing waveform of the selected tissue of the subject, and outputs the initializing pulses corresponding to the initialization timings.

4. The ultrasonic diagnostic apparatus according to claim 1, further comprising a selection unit that analyzes Doppler shifts of a plurality of received signals to select one from a plurality of tissues of the subject,
wherein the detection unit detects the initialization timings by analyzing the tissue tracing waveform of the selected tissue of the subject, and outputs the initializing pulses corresponding to the initialization timings.

5. The ultrasonic diagnostic apparatus according to claim 1, further comprising: a tissue property calculating unit that calculates a tissue property of the subject based on the tissue tracing waveform; and a selection unit that analyzes the tissue property of the subject to select one from a plurality of tissues of the subject,
wherein the detection unit detects the initialization timings by analyzing the tissue tracing waveform of the selected tissue of the subject, and outputs the initializing pulses corresponding to the initialization timings.

6. The ultrasonic diagnostic apparatus according to claim 1, further comprising a switching unit that switches between an initializing operation of initializing the tissue tracing waveform based on the initializing pulses and an initializing operation of initializing the tissue tracing waveform by a signal that is in synchronization with a heartbeat, the signal being taken from a heartbeat information measurement unit that measures heartbeat information including an electrocardiogram or a cardiac sound.

7. The ultrasonic diagnostic apparatus according to claim 1, further comprising a tissue property calculating unit that calculates a tissue property of the subject based on tissue tracing waveforms of a plurality of tissues of the subject.

8. The ultrasonic diagnostic apparatus according to claim 1, further comprising a delay unit that delays the initialization pulses for a predetermined delay time,
wherein the tissue tracing unit is initialized by the delayed initializing pulses.

9. The ultrasonic diagnostic apparatus according to claim 8, wherein the predetermined delay time is estimated from several immediately preceding heartbeat intervals.

10. The ultrasonic diagnostic apparatus according to claim 1,
wherein the detection unit outputs each of the initializing pulses for each heartbeat of the subject, respectively.

11. The ultrasonic diagnostic apparatus according to claim 1,
wherein each tissue tracing wave unit is corresponding to each heartbeat of the subject.

12. An ultrasonic diagnostic apparatus, comprising:
an ultrasonic wave transmitter that transmits an ultrasonic wave to a subject;
an ultrasonic wave receiver that receives the ultrasonic wave from the subject and outputs a received signal based upon the received ultrasonic wave;
a tissue tracing unit that generates a tissue tracing waveform by analyzing the received signal supplied from the ultrasonic wave receiver, said tissue tracing waveform including a waveform that traces a position of a tissue of the subject;
a detection unit that detects initialization timings by analyzing a change in an amplitude or a phase of the received signal supplied from the ultrasonic wave receiver without using information from an electrocardiograph, and outputs initializing pulses corresponding to the initialization timings,
wherein said tissue tracing unit is repeatedly initialized based on the initialization pulses.

13. The ultrasonic diagnostic apparatus according to claim 12, further comprising a delay unit that delays the initialization pulses for a predetermined delay time, wherein the tissue tracing unit is initialized by the delayed initializing pulses.

14. The ultrasonic diagnostic apparatus according to claim 13, wherein the predetermined delay time is estimated from several immediately preceding heartbeat intervals.

15. The ultrasonic diagnostic apparatus according to claim 12,
wherein the detection unit outputs each of the initializing pulses for each heartbeat of the subject, respectively.

16. The ultrasonic diagnostic apparatus according to claim 12,
wherein each tissue tracing wave unit is corresponding to each heartbeat of the subject.

17. An ultrasonic diagnostic apparatus, comprising:
an ultrasonic wave transmitter that transmits an ultrasonic wave to a subject;
an ultrasonic wave receiver that receives the ultrasonic wave from the subject and outputs a received signal based upon the received ultrasonic wave;
a delay unit that outputs a delayed received signal by delaying a received signal from the ultrasonic wave receiver;
a tissue tracing unit that generates a delayed tissue tracing waveform and a not-delayed tissue tracing waveform by analyzing the delayed received signal from the delay unit and the received signal from the ultrasonic wave receiver, said delayed tissue tracing waveform including a waveform that traces a position of a tissue of the subject; and
a detection unit that detects initialization timings by analyzing a change to an aspect of the not-delayed tissue tracing waveform without using information from an electrocardiograph, and outputs initializing pulses corresponding to the initialization timings,
wherein said tissue tracing unit is repeatedly initialized based on the initialization pulses.

18. The ultrasonic diagnostic apparatus according to claim 17,
wherein the detection unit outputs each of the initializing pulse for each heartbeat of the subject, respectively.

19. The ultrasonic diagnostic apparatus according to claim 17,
wherein each tissue tracing wave unit is corresponding to each heartbeat of the subject.

20. An ultrasonic diagnostic apparatus, comprising:
an ultrasonic wave transmitter that transmits an ultrasonic wave to a subject;
an ultrasonic wave receiver that receives the ultrasonic wave from the subject and outputs a received signal based upon the received ultrasonic wave;
a delay unit that outputs a delayed received signal by delaying a received signal from the ultrasonic wave receiver;
a tissue tracing unit that generates a delayed tissue tracing waveform by analyzing the delayed received signal from the delay unit, said delayed tissue tracing waveform including a waveform that traces a position of a tissue of the subject; and
a detection unit that detects initialization timings by analyzing a change to an amplitude or a phase of the received signal supplied from the ultrasonic wave receiver without using information from an electrocardiograph, and outputs initializing pulses corresponding to the initialization timings,
wherein said tissue tracing unit is repeatedly initialized based on the initialization pulses.

21. The ultrasonic diagnostic apparatus according to claim 20,
wherein the detection unit outputs each of the initializing pulses for each heartbeat of the subject, respectively.

22. The ultrasonic diagnostic apparatus according to claim 20,
wherein each tissue tracing wave unit is corresponding to each heartbeat of the subject.

* * * * *